US009421240B2

(12) United States Patent
Francois et al.

(10) Patent No.: US 9,421,240 B2
(45) Date of Patent: Aug. 23, 2016

(54) COMPSTATIN ANALOGS FOR TREATMENT OF NEUROPATHIC PAIN

(75) Inventors: Cedric Francois, Louisville, KY (US); Pascal Deschatelets, Louisville, KY (US)

(73) Assignee: Apellis Pharmaceuticals, Inc., Crestwood, KY (US)

( * ) Notice: Subject to any disclaimer, the term of this patent is extended or adjusted under 35 U.S.C. 154(b) by 356 days.

(21) Appl. No.: 13/805,538

(22) PCT Filed: Jun. 22, 2011

(86) PCT No.: PCT/US2011/041492
§ 371 (c)(1),
(2), (4) Date: Apr. 10, 2013

(87) PCT Pub. No.: WO2011/163394
PCT Pub. Date: Dec. 29, 2011

(65) Prior Publication Data
US 2013/0203678 A1    Aug. 8, 2013

Related U.S. Application Data

(60) Provisional application No. 61/357,448, filed on Jun. 22, 2010.

(51) Int. Cl.
| A61K 38/04 | (2006.01) |
| A61K 38/12 | (2006.01) |
| A61K 38/10 | (2006.01) |
| A61F 13/532 | (2006.01) |
| A61F 13/535 | (2006.01) |
| A61K 45/06 | (2006.01) |
| A61F 13/53 | (2006.01) |

(52) U.S. Cl.
CPC .............. *A61K 38/10* (2013.01); *A61F 13/532* (2013.01); *A61F 13/535* (2013.01); *A61K 38/12* (2013.01); *A61K 45/06* (2013.01); *A61F 2013/530554* (2013.01)

(58) Field of Classification Search
None
See application file for complete search history.

(56) References Cited

U.S. PATENT DOCUMENTS

| 5,492,135 | A | 2/1996 | DeVore et al. |
| 5,861,486 | A | 1/1999 | Devore et al. |
| 6,129,761 | A | 10/2000 | Hubbell |
| 6,197,934 | B1 | 3/2001 | DeVore et al. |
| 6,204,365 | B1 | 3/2001 | Devore et al. |
| 6,319,897 | B1 | 11/2001 | Lambris et al. |
| 6,897,290 | B1 | 5/2005 | Atkinson et al. |
| 7,084,106 | B1 | 8/2006 | Kotwal et al. |
| 7,108,982 | B1 | 9/2006 | Hageman |
| 7,888,323 | B2 | 2/2011 | Lambris et al. |
| 7,989,589 | B2 | 8/2011 | Lambris |
| 8,168,584 | B2 | 5/2012 | Deschatelets et al. |
| 2002/0102581 | A1 | 8/2002 | Hageman et al. |
| 2003/0017501 | A1 | 1/2003 | Hageman et al. |
| 2003/0207309 | A1 | 11/2003 | Hageman et al. |
| 2005/0222027 | A1 | 10/2005 | Chiang et al. |
| 2005/0287601 | A1 | 12/2005 | Hageman et al. |
| 2006/0002852 | A1 | 1/2006 | Saltzman et al. |
| 2006/0002971 | A1 | 1/2006 | Saltzman et al. |
| 2006/0142191 | A1 | 6/2006 | Francois et al. |
| 2006/0257359 | A1 | 11/2006 | Francois et al. |
| 2006/0263819 | A1 | 11/2006 | Hageman et al. |
| 2007/0020647 | A1 | 1/2007 | Hageman et al. |
| 2007/0149616 | A1 | 6/2007 | Clark et al. |
| 2007/0196367 | A1 | 8/2007 | Dinu |
| 2008/0075755 | A1 | 3/2008 | Deschatelets et al. |
| 2010/0166862 | A1 | 7/2010 | Francois et al. |
| 2011/0092446 | A1 | 4/2011 | Francois et al. |
| 2011/0182877 | A1 | 7/2011 | Francois et al. |
| 2012/0135430 | A1 | 5/2012 | Zhang et al. |

FOREIGN PATENT DOCUMENTS

| JP | 11-197234 A | 7/1999 |
| WO | WO-97/33603 A1 | 9/1997 |
| WO | WO-99/13899 A1 | 3/1999 |
| WO | WO-00/47130 A9 | 8/2000 |
| WO | WO-01/84149 A3 | 11/2001 |
| WO | WO-03/047633 A3 | 10/2003 |
| WO | WO-03/086448 A1 | 10/2003 |
| WO | WO-2004/026328 A1 | 4/2004 |
| WO | WO-2004/037310 A3 | 5/2004 |
| WO | WO-2004/041160 A3 | 5/2004 |
| WO | WO-2006/042329 A8 | 4/2006 |
| WO | WO-2006/062716 A3 | 6/2006 |
| WO | WO-2006/080951 A8 | 8/2006 |
| WO | WO-2006/099330 A3 | 9/2006 |
| WO | WO-2007/056227 A3 | 5/2007 |
| WO | WO-2007/062249 A3 | 5/2007 |
| WO | WO-2007/076437 A3 | 7/2007 |
| WO | WO-2007/084765 A3 | 7/2007 |
| WO | WO-2009/015087 | 1/2009 |
| WO | WO-2012/006599 A2 | 1/2012 |
| WO | WO-2012/178083 A1 | 12/2012 |

OTHER PUBLICATIONS

Wells, J.A. (1990). Additivity of mutational effects in proteins. Biochemistry. 29(37):8509-8517.*

(Continued)

*Primary Examiner* — Christine J Saoud
*Assistant Examiner* — Jon M Lockard
(74) *Attorney, Agent, or Firm* — Choate, Hall & Stewart, LLP; Brenda H. Jarrell; Suzanne Nguyen

(57) ABSTRACT

In some aspects, the present invention provides methods of treating a subject in need of treatment for neuropathic pain, the method comprising administering a compstatin analog to the subject. In some embodiments, the compstatin analog is administered parenterally, e.g., intravenously.

9 Claims, No Drawings

(56) References Cited

OTHER PUBLICATIONS

Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*

International Preliminary Report on Patentability for PCT/US2011/041492, mailed Jan. 10, 2013.

Acosta, J. et al., Complement and complement regulatory proteins as potential molecular targets for vascular diseases, Curr Pharm Des, 10(2):203-211, Bentham Science Publishers Ltd., Bussum, the Netherlands (2004).

Acosta, J. et al., Molecular basis for a link between complement and the vascular complications of diabetes, Proc. Nat. Acad. Sci., 97(10):5450, National Academies of Science, Washington, DC (2000).

Anderson, D.H. et al., A role for local inflammation in the formation of drusen in the aging eye, Am J Ophthalmol, 134:411-431 (2002).

Bora, P.S. et al., Complement activation by alternative pathway is critical in the development of laser-induced choroidal neovascularization, Invest Ophthalmol Vis Sci, 47:E-Abstract 4167, Association for Research in Vision and Ophthalmology, Rockville, MD (2006).

Bora, P.S. et al., Complement Activation is Required in the Murine Model of Laser-induced Choroidal Neovascularization, Invest Ophthalmol Vis Sci, 44:E-Abstract 3940, Association for Research in Vision and Ophthalmology, Rockville, MD (2003).

Bora, P.S. et al., Neovascularization in a mouse model that simulates exudative macular degeneration is complement dependent, Invest Ophthalmol Vis Sci, 45:E-Abstract 1871, Association for Research in Vision and Ophthalmology, Rockville, MD (2004).

Bora, P.S. et al., Role of complement and complement membrane attack complex in neovascularization, Journal of Immunology, 174(1):491-497, American Association of Immunologists, Bethesda, MD (2005).

Bora, P.S. et al., Role of complement system in choroidal neovascularization, Invest Ophthalmol Vis Sci, 43: E-Abstract 1291. Association for Research in Vision and Ophthalmology, Rockville, MD. (2002).

Braun, J., Daily Nexus, 83(135):1-5 (2003).

Campbell, J.N. et al., Mechanisms of Neuropathic Pain, Neuron., 52(1):77-92 (2006).

Conley, Y.P. et al., Candidate gene analysis suggests a role for fatty acid biosynthesis and regulation of the complement system in the etiology of age-related maculopathy, Hum Mol Genet, 14:1991-2002 (2005).

Costigan, M. et al., Neuropathic pain: a maladaptive response of the nervous system to damage, Annu. Rev. Neurosci., 32:1-32 (2009).

Davenport, R.J., Sci. Aging Knowl. Environ, 2004(37):85 (2004).

Donoso, L. et al., The role of inflammation in the pathogenesis of age-related macular degeneration, Survey of Ophthalmology, 51(2):137-152, Elsevier Inc., Amsterdam, Netherlands (2006).

Edwards, A.O. et al., Complement Factor H Polymorphism and Age-Related Macular Degeneration, Science, 308(5720):421-424, American Association for the Advancement of Science, Washington, DC (2005).

Griffin, R.S. et al., Complement induction in spinal cord microglia results in anaphylatoxin C5a-mediated pain Hypersensitivity, J. Neurosci., 27(32):8699-8708 (2007).

Haines, J.L. et al., Complement factor H variant increases the risk of age-related macular degeneration, Science, 308(5720):419-421, American Association for the Advancement of Science, Washington, DC (2005).

Holland, M.C.H., et al., Synthetic small-molecule complement inhibitors, Curr Op Invest Drugs, 5(11):1164-1173, The Thomson Corporation (2004).

ISR_and_Written_Opinion for PCT/US2011/041492, dated Feb. 23, 2012.

Jha, P. et al., The complement system plays a critical role in the development of experimental autoimmune anterior uveitis, Investigative Ophthalmology and Visual Sciences, 47(3):1030-1038, Association for Research in Vision and Ophthalmology, Rockville, MD (2006).

Johnson, L.V. et al., Complement activation and inflammatory processes in drusen formation and age related macular degeneration, Experimental Eye Research, 73(6):887-896, Academic Press Ltd., London, GB (2001).

Katragadda and Lambris, Expression of compstatin in *Escherichia coli*: Incorporation of unnatural amino acids enhances its activity, Protein Expression and Purification, 47(1):289-295, Academic Press, San Diego, CA (2006).

Katragadda et al., Hydrophobic effect and hydrogen bonds account for the improved activity of a complement inhibitor, compstatin, Journal of Medicinal Chemistry, 49(15):4616-4622, American Chemical Society, Washington, DC (2006).

Katragadda et al., Structure-activity-based design of potent compstatin analogs, Molecular Immunology, 44(1-3):192, Elsevier, Elmsford, NY (2007).

Katragadda et al., Thermodynamic studies on the interaction of the third complement component and its inhibitor, compstatin, Journal of Biological Chemistry, 279(53):54987-54995, American Society for Biochemistry and Molecular Biology, Bethesda, MD (2004).

Klein, R.J. et al., Complement Factor H Polymorphism in Age-Related Macular Degeneration, Science, 308(5720):385-389, American Association for the Advancement of Science, Washington, DC (2005).

Leung, L. et al., TNF-Alpha and neuropathic pain—a review, J. Neuroinflammation, 7::27, 11 pages (2010).

Levin, M.E. et al., Complement activation in the peripheral nervous system following the spinal nerve ligation model of neuropathic pain, Pain, 137:182-201 (2008).

Li, M. et al., Complement activation contributes to leukocyte recruitment and neuropathic pain following peripheral nerve injury in rats, Eur. J. Neurosci., 26:3486-3500 (2007).

Makrides, S.C. et al., Therapeutic inhibition of the complement system, Pharmacological Reviews, 50(1):59-87, American Society for Pharmacology and Experimental Therapeutics, Bethesda, MD (1998).

Maller, J. et al., Common variation in three genes, including a noncoding variant in CFH, strongly influences risk of age-related macular degeneration, Nature Genetics, 38(9):1055-1059, Nature Publishing Group, New York, NY (2006).

Mallik, B. et al., Design and NMR characterization of active analogues of compstatin containing non-natural amino acids, Journal of Medicinal Chemistry, 48 (1):274-286 (2005).

Mika, J., Modulation of microglia can attenuate neuropathic pain symptoms and enhance morphine effectiveness, Pharmacological Reports, 60:297-307 (2008).

Morikis, D. et al., Improvement of the anti-C3 activity of compstatin using rational and combinatorial approaches, Biochemical Society Transactions, 32(1):28-32, Biochemical Society, London, UK (2004).

Nozaki, M. et al., Drusen complement components C3a and C5a promote choroidal neovascularization, Proc Natl Acad Sci U S A, 103:2328-2333, National Academies of Science, Washington, DC (2006).

Sahu, A. et al., Binding kinetics, structure-activity relationship, and biotransformation of the complement inhibitor compstatin, J Immunol, 165(5):2491-2499, The American Association of Immunologists, Bethesda, MD. (2000).

Sahu, A. et al., Compstatin, a peptide inhibitor of complement, exhibits species-specific binding to complement component C3, Mol Immunol, 39(10):557-566, Elsevier, Elmsford, NY (2003).

Scholz, J. et al., The Neuropathic pain triad: neurons, immune cells and glia, Nat. Neurosci.,10(11):1361-13688 (2007).

Sepp, T. et al., Complement Factor H Variant Y402H Is a Major Risk Determinant for Geographic Atrophy and Choroidal Neovascularization in Smokers and Nonsmokers, Invest Ophthalmol Vis Sci, 47:536-540, Association for Research in Vision and Ophthalmology, Rockville, MD (2006).

Sivaprasad, S. and Chong, N.V., The complement system and age-related macular Degeneration, Eye, 20:867-872, The Nature Publishing Group, New York, NY (2006).

(56) References Cited

OTHER PUBLICATIONS

Soulika, A.M. et al., Studies of structure-activity relations of complement inhibitor compstatin, J Immunol, 171(4):1881-1890, The American Association of Immunologists, Bethesda, MD (2003).

Twining, C.M. et al., Peri-sciatic proinflammatory cytokines, reactive oxygen species, and complement induce mirror-image neuropathic pain in rats, Pain, 110:299-309 (2004).

Yates, J.R.W. et al., Complement C3 variant and the risk of age-related macular degeneration, N Engl J Med, 357(6):553-561, Massachusetts Medical Society (2007).

Zhang et al., Early complement activation and decreased levels of glycosylphosphatidylinositol-anchored complement inhibitors in human and experimental diabetic retinopathy, Diabetes, 51(12):3499-3504, American Diabetes Association, Washington, DC (2002).

Zhou et al., Complement Activation by Bisretinoid Constituents of RPE Lipofuscin, Invest Ophthalmol Vis Sci, 50:1392-1399 (2009).

Zhou, J. et al., Complement activation by photooxidation products of A2E, a lipofuscin constituent of the retinal pigment epithelium, Proc Natl Acad Sci USA, 103:16182-16187, National Academies of Science, Washington, DC. (2006).

* cited by examiner

COMPSTATIN ANALOGS FOR TREATMENT OF NEUROPATHIC PAIN

CROSS-REFERENCE TO RELATED APPLICATIONS

This application is a national phase entry of International Application No. PCT/US2011/041492, filed Jun. 22, 2011, which claims the benefit of an priority to U.S. Provisional Patent Application 61/357,448, filed Jun. 22, 2010, the entire contents of both of which are incorporated herein by reference.

SEQUENCE LISTING

The present specification makes reference to a Sequence Listing (submitted electronically as a .txt file named "2008575-0042_Sequence_Listing.txt" on Nov. 5, 2015). The .txt file was generated on Nov. 5, 2015 and is 20,418 bytes in size. The entire contents of the Sequence Listing are herein incorporated by reference.

BACKGROUND OF THE INVENTION

Pain is a major symptom in many medical conditions and a common reason that prompts individuals to seek medical attention. Neuropathic pain is a type of pain that may arise as a consequence of a lesion or disease affecting the somatosensory system. Neuropathic pain is typically characterized by patients as burning, aching, or shooting. The pain may be provoked by normally innocuous stimuli (allodynia). It is also commonly associated with hyperalgesia (increased pain intensity evoked by normally painful stimuli) and abnormal sensations, such as pins-and-needles or electric-shock-like sensations. Neuropathic pain can be very severe and disabling and can result in significant functional, psychological, and/or social consequences.

Neuropathic pain has been estimated to affect up to 6%-8% of the general population. It can arise from a variety of causes that involve the brain, spinal cord, and/or peripheral nerves, including cervical or lumbar radiculopathy, diabetic neuropathy, postherpetic neuralgia, HIV-related neuropathy, and spinal cord injury, among others. Neuropathic pain can arise following physical injury, persisting despite resolution of the inciting damage to the nerve and the surrounding tissues.

Regardless of the underlying cause of neuropathic pain, common treatment goals are to decrease pain and/or improve function. Tricyclic antidepressants, anticonvulsants, and opioid analgesics are frequently prescribed. However, these medications frequently fail to provide adequate pain relief and/or are associated with troubling side effects. People with neuropathic pain have been found to generate 3-fold higher health care costs compared with matched controls. In the United States, health care, disability and related costs associated with neuropathic pain have been estimated at almost $40 billion annually.

There is a considerable need for more effective pharmacological therapies for neuropathic pain.

SUMMARY OF THE INVENTION

The invention provides a method of treating a subject suffering from neuropathic pain, the method comprising administering a compstatin analog to the subject. In some embodiments the compstatin analog is administered parenterally, e.g., intravenously. In some embodiments, the subject suffers from painful diabetic neuropathy, post-herpetic neuralgia, trigeminal neuralgia, cancer related neuropathic pain, chemotherapy-associated neuropathic pain, HIV related neuropathic pain (e.g., from HIV neuropathy), central/post-stroke neuropathic pain, neuropathy associated with back pain, e.g., low back pain (e.g, from radiculopathy such as spinal root compression, e.g., lumbar root compression), peripheral nerve injury pain, phantom limb pain, polyneuropathy, spinal cord injury related pain, myelopathy, and/or multiple sclerosis. All articles, books, patent applications, patents, other publications, and electronic databases mentioned in this application are incorporated herein by reference. In the event of a conflict between the specification and any of the incorporated references the specification (including any amendments thereto) shall control. Unless otherwise indicated, art-accepted meanings of terms and abbreviations are used herein.

DEFINITIONS

The terms "approximately" or "about" in reference to a number generally include numbers that fall within ±10%, in some embodiments ±5%, in some embodiments ±1%, in some embodiments ±0.5% of the number unless otherwise stated or otherwise evident from the context (except where such number would impermissibly exceed 100% of a possible value).

A "complement component" or "complement protein" is a protein that is involved in activation of the complement system or participates in one or more complement-mediated activities. Components of the classical complement pathway include, e.g., C1q, C1r, C1s, C2, C3, C4, C5, C6, C7, C8, C9, and the C5b-9 complex, also referred to as the membrane attack complex (MAC) and active fragments or enzymatic cleavage products of any of the foregoing (e.g., C3a, C3b, C4a, C4b, C5a, etc.). Components of the alternative pathway include, e.g., factors B, D, and properdin. Components of the lectin pathway include, e.g., MBL2, MASP-1, and MASP-2. Complement components also include cell-bound receptors for soluble complement components, wherein such receptor mediates one or more biological activities of such soluble complement component following binding of the soluble complement component. Such receptors include, e.g., C5a receptor (C5aR), C3a receptor (C3aR), Complement Receptor 1 (CR1), Complement Receptor 2 (CR2), Complement Receptor 3 (CR3, also known as CD45), etc. It will be appreciated that the term "complement component" is not intended to include those molecules and molecular structures that serve as "triggers" for complement activation, e.g., antigen-antibody complexes, foreign structures found on microbial or artificial surfaces, etc.

A "complement regulatory protein" is a protein involved in regulating complement activity. A complement regulatory protein may down-regulate complement activity by, e.g., inhibiting complement activation or by inactivating or accelerating decay of one or more activated complement proteins. Examples of complement regulatory proteins include C1 inhibitor, C4 binding protein, clusterin, vitronectin, CFH, factor I, and the cell-bound proteins CD46, CD55, CD59, CR1, CR2, and CR3.

"Linked", as used herein with respect to two or more moieties, means that the moieties are physically associated or connected with one another to form a molecular structure that is sufficiently stable so that the moieties remain associated under the conditions in which the linkage is formed and, preferably, under the conditions in which the new molecular structure is used, e.g., physiological conditions. In certain preferred embodiments of the invention the linkage is a covalent linkage. In other embodiments the linkage is noncovalent. Moieties may be linked either directly or indirectly. When two moieties are directly linked, they are either covalently bonded to one another or are in sufficiently close proximity such that intermolecular forces between the two moieties maintain their association. When two moieties are indirectly linked, they are each linked either covalently or noncovalently to a third moiety, which maintains the association between the two moieties. In general, when two moieties are referred to as being linked by a "linking moiety" or "linking portion", the linkage between the two linked moieties is indirect, and typically each of the linked moieties is covalently bonded to the linking moiety. Two moieties may be linked using a "linker". A linker can be any suitable moiety that reacts with the entities to be linked within a reasonable period of time, under conditions consistent with stability of the entities (portions of which may be protected as appropriate, depending upon the conditions), and in sufficient amount, to produce a reasonable yield. Typically the linker will contain at least two functional groups, one of which reacts with a first entity and the other of which reacts with a second entity. It will be appreciated that after the linker has reacted with the entities to be linked, the term "linker" may refer to the part of the resulting structure that originated from the linker, or at least the portion that does not include the reacted functional groups. A linking moiety may comprise a portion that does not participate in a bond with the entities being linked, and whose main purpose may be to spatially separate the entities from each other. Such portion may be referred to as a "spacer".

"Polypeptide", as used herein, refers to a polymer of amino acids, optionally including one or more amino acid analogs. A protein is a molecule composed of one or more polypeptides. A peptide is a relatively short polypeptide, typically between about 2 and 60 amino acids in length, e.g., between 8 and 40 amino acids in length. The terms "protein", "polypeptide", and "peptide" may be used interchangeably. Polypeptides used herein may contain amino acids such as those that are naturally found in proteins, amino acids that are not naturally found in proteins, and/or amino acid analogs that are not amino acids. As used herein, an "analog" of an amino acid may be a different amino acid that structurally resembles the amino acid or a compound other than an amino acid that structurally resembles the amino acid. A large number of art-recognized analogs of the 20 amino acids commonly found in proteins (the "standard" amino acids) are known. One or more of the amino acids in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. Certain non-limiting suitable analogs and modifications are described in WO2004026328. The polypeptide may be acetylated, e.g., at the N-terminus and/or amidated, e.g., at the C-terminus "Reactive functional groups" as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those frequently used to prepare bioconjugates, e.g., N-hydroxysuccinimide esters, maleimides, sulfhydryls, and the like (see, for example, Hermanson, G., *Bioconjugate Techniques*, Academic press, San Diego, 1996 or the second edition thereof, published in 2008, Elsevier). Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

A "subject" treated according to the instant invention is typically a human, a non-human primate, or a lower animal (e.g., a mouse or rat), which expresses or contains at least some primate (e.g., human) complement component C3 and, optionally, one or more additional primate complement component(s). In some embodiments the subject is male. In some embodiments the subject is female. In some embodiments the subject is an adult, e.g., a human at least 18 years of age, e.g., between 18 and 100 years of age.

As used herein, "alkyl" refers to a saturated straight, branched, or cyclic hydrocarbon having from about 1 to about 22 carbon atoms (and all combinations and subcombinations of ranges and specific numbers of carbon atoms therein), with from about 1 to about 12, or about 1 to about 7 carbon atoms being preferred in certain embodiments of the invention. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "halo" refers to F, Cl, Br or I.

As used herein, "alkanoyl" refers to an optionally substituted straight or branched aliphatic acyclic residue having about 1 to 10 carbon atoms (and all combinations and subcombinations of ranges and specific number of carbon atoms) therein, e.g., from about 1 to 7 carbon atoms. Alkanoyl groups include, but are not limited to, formyl, acetyl, propionyl, butyryl, isobutyryl, pentanoyl, isopentanoyl, 2-methyl-butyryl, 2,2-dimethoxypropionyl, hexanoyl, heptanoyl, octanoyl, and the like. "Lower alkanoyl" refers to an optionally substituted straight or branched aliphatic acyclic residue having about 1 to about 5 carbon atoms (and all combinations and subcombinations of ranges and specific number of carbon atoms). Such groups include, but are not limited to, formyl, acetyl, propionyl, butyryl, isobutyryl, pentanoyl, isopentanoyl, etc.

As used herein, "aryl" refers to an optionally substituted, mono- or bicyclic aromatic ring system having from about 5 to about 14 carbon atoms (and all combinations and subcombinations of ranges and specific numbers of carbon atoms therein), with from about 6 to about 10 carbons being preferred. Non-limiting examples include, for example, phenyl and naphthyl.

As used herein, "aralkyl" refers to alkyl radicals bearing an aryl substituent and have from about 6 to about 22 carbon atoms (and all combinations and subcombinations of ranges and specific numbers of carbon atoms therein), with from about 6 to about 12 carbon atoms being preferred in certain embodiments. Aralkyl groups can be optionally substituted. Non-limiting examples include, for example, benzyl, naphthylmethyl, diphenylmethyl, triphenylmethyl, phenylethyl, and diphenylethyl.

As used herein, the terms "alkoxy" and "alkoxyl" refer to an optionally substituted alkyl-O— group wherein alkyl is as previously defined. Exemplary alkoxy and alkoxyl groups include methoxy, ethoxy, n-propoxy, i-propoxy, n-butoxy, and heptoxy.

As used herein, "carboxy" refers to a —C(=O)OH group.

As used herein, "alkoxycarbonyl" refers to a —C(=O)O-alkyl group, where alkyl is as previously defined.

As used herein, "aroyl" refers to a —C(=O)-aryl group, wherein aryl is as previously defined. Exemplary aroyl groups include benzoyl and naphthoyl.

Typically, substituted chemical moieties include one or more substituents that replace hydrogen. Exemplary substituents include, for example, halo, alkyl, cycloalkyl, aralkyl, aryl, sulfhydryl, hydroxyl (—OH), alkoxyl, cyano (—CN), carboxyl (—COOH), —C(=O)O-alkyl, aminocarbonyl (—C(=O)NH$_2$), —N-substituted aminocarbonyl (—C(=O)NHR"), CF$_3$, CF$_2$CF$_3$, and the like. In relation to the aforementioned substituents, each moiety R" can be, independently, any of H, alkyl, cycloalkyl, aryl, or aralkyl, for example.

As used herein, "L-amino acid" refers to any of the naturally occurring levorotatory alpha-amino acids normally present in proteins or the alkyl esters of those alpha-amino acids. The term D-amino acid" refers to dextrorotatory alpha-amino acids. Unless specified otherwise, all amino acids referred to herein are L-amino acids.

As used herein, an "aromatic amino acid" is an amino acid that comprises at least one aromatic ring, e.g., it comprises an aryl group.

As used herein, an "aromatic amino acid analog" is an amino acid analog that comprises at least one aromatic ring, e.g., it comprises an aryl group.

DETAILED DESCRIPTION OF CERTAIN EMBODIMENTS OF THE INVENTION

The present invention provides compositions and methods for treating a subject suffering from neuropathic pain. In one aspect the invention provides a method of treating a subject suffering from neuropathic pain, the method comprising administering a compstatin analog to the subject. As described in further detail below, compstatin analogs are complement inhibitors that bind to complement component C3 and inhibit its cleavage, thus inhibiting complement activation via the three major complement activation pathways. Compstatin analogs are highly effective in reducing formation of complement system effectors. The invention encompasses the recognition of the benefit of compstatin analogs for treatment of neuropathic pain.

Neuropathic pain has been defined as pain initiated or caused by a primary lesion or dysfunction in the nervous system, in particular, pain arising as a direct consequence of a lesion or disease affecting the somatosensory system. For example, neuropathic pain may arise from lesions that involve the somatosensory pathways with damage to small fibres in peripheral nerves and/or to the spino-thalamocortical system in the CNS. Neuropathic pain is considered to arise at least in part from mechanisms other than as a direct result of stimulation of peripheral sensory endings by actually or potentially tissue-damaging stimuli. Neuropathic pain can occur because of dysfunction or disease of the nervous system at the peripheral and/or central level. Neuropathic pain may be classified by etiology and/or by the presumed or demonstrated site of neurologic involvement (central or peripheral). However, both peripheral and central nervous system lesions may contribute to many types of neuropathic pain. Neuropathic pain can be chronic, e.g., lasting for at least 3, 6, 9, 12, 24, 36 months, or more, e.g., as measured from the onset of the pain. It can be spontaneous (stimulus-independent or spontaneous pain) or elicited by a stimulus (stimulus-dependent or stimulus-evoked pain). Spontaneous neuropathic pain is often described as a constant burning sensation, but it may also include intermittent shooting, lancinating sensations, electric shock-like pain, and/or dysesthesias (i.e. abnormal and unpleasant sensations). It will be appreciated that neuropathic pain can be continuous or intermittent and may wax and wane during a time interval. It can be associated with allodynia, hyperalgesia, and/or paresthesias. In some embodiments of the invention, a compstatin analog is administered to treat a subject with neuropathic pain associated with an identified neurologic lesion. A neurologic lesion can be identified based on neurological examination, laboratory tests, and/or imaging studies, etc., and can take into account the existence of a disease (e.g., diabetes, HIV), known to be associated with nerve damage.

Neuropathic pain can arise from autoimmune disease (e.g., multiple sclerosis), metabolic diseases (e.g., diabetes), infection (e.g., viral diseases such as shingles), vascular disease (e.g., stroke), trauma (e.g., injury, surgery), and cancer. For example, neuropathic pain can be pain that persists after healing of an injury or after cessation of a stimulus of peripheral nerve endings or pain that arises due to damage to nerves. Exemplary conditions of or associated with neuropathic pain include painful diabetic neuropathy, post-herpetic neuralgia (e.g., pain persisting or recurring at the site of acute herpes zoster 3 or more months after the acute episode), trigeminal neuralgia, cancer related neuropathic pain, chemotherapy-associated neuropathic pain, HIV-related neuropathic pain (e.g., from HIV neuropathy), central/post-stroke neuropathic pain, neuropathy associated with back pain, e.g., low back pain (e.g., from radiculopathy such as spinal root compression, e.g., lumbar root compression, which compression may arise due to disc herniation), spinal stenosis, peripheral nerve injury pain, phantom limb pain, polyneuropathy, spinal cord injury related pain, myelopathy, and multiple sclerosis. In certain embodiments of the invention a compstatin analog is administered to treat neuropathic pain in a subject with one or more of the afore-mentioned conditions.

Neuropathic pain can be diagnosed using methods known in the art such as, but not limited to, medical/surgical history and/or neurologic examination. A neurological examination that includes an accurate sensory examination is often sufficient to reach a diagnosis in the clinical setting. Nerve conduction studies and somatosensory-evoked potentials may be used to demonstrate and/or localize a peripheral or central nervous lesion. It will be appreciated that the diagnosis of neuropathic pain is within the discretion of the skilled practitioner. A variety of clinical tools are available that can be used to assess pain characteristics and, if desired, to determine whether a subject has chronic pain of predominantly neuropathic origin. Such tools can be based on questions (eliciting descriptions of the pain) and/or physical tests. For example, the Leeds Assessment of Neuropathic Symptoms and Signs pain scale (LANSS) was developed as a clinic based instrument for identifying patients whose pain is dominated by neuropathic mechanisms (Bennett M: The LANSS Pain Scale: the Leeds assessment of neuropathic symptoms and signs. Pain 92:147-157, 2001). It has been validated and is also available as a self-complete version, the S-LANSS, which was found to be valid and reliable at identifying chronic pain of predominantly neuropathic origin (POPNO) on the basis of the patient's current symptoms and signs in comparison with expert clinical judgement (Bennett M I, et al. The S-LANSS score for identifying pain of predominantly neuropathic origin: validation for use in clinic and postal research. *J Pain.* 6:149-158, 2005; see also Torrance, N, et al., The Journal of Pain, 7(4): 281-289, 2006). The DN4 is another assessment tool that allows identification of chronic pain with neuropathic characteristics with a very good specificity and sensitivity (Bouhassira D, et al. Comparison of pain syndromes associated with nervous or somatic lesions and development of a new neuropathic pain diagnostic questionnaire (DN4). *Pain.* 114:29-36, 2005; see also Bouhassira D, et al. Pain 136, 380-387, 2008). It consists of seven interview questions and three physical tests. Administration of the DN4 interview alone can be used to identify subjects with POPNO. Another assessment tool that could be used to distinguish between neuropathic and non-neuropathic pain, in particular low back pain, and/or to classify subjects is the Standardized Evaluation of Pain (StEP) (Scholz, J. et al., *PLoS Med.* A novel tool for the assessment of pain: validation in low back pain, 2009). In some embodiments, a compstatin analog is administered to treat a subject suffering from chronic pain that has characteristics of neuropathic pain (e.g., based on pain descriptors) and/or physical test(s). In some embodiments, the subject has pain that meets the criteria for POPNO based on an assessment tool such as the LANNS, S-LANNS, or DN4. In some embodiments, the subject has POPNO and lacks an identified nervous system lesion. In some embodiments, the subject has POPNO and the pain is associated with an identified nervous system lesion. In some embodiments, a compstatin analog is used to treat a subject with moderate or severe pain, based on a pain intensity score (discussed further below). In some embodiments, the intensity is at least 6 on a 0-10 point scale (discussed further below). In some embodiments, a compstatin analog is used to treat a subject in need of treatment for neuropathic pain, e.g., a subject suffering from neuropathic pain or a condition associated with neuropathic pain, wherein the subject has not been diagnosed with and/or does not also suffer from a different disorder or condition for which compstatin analog treatment would be appropriate and/or wherein the subject is not being treated with a compstatin analog for such a disorder or condition. In some embodiments, a compstatin analog is used to treat a subject in need of treatment for neuropathic pain, e.g., a subject suffering from neuropathic pain or a condition associated with neuropathic pain, wherein the subject has been diagnosed with and/or also suffers from a different disorder or condition for which compstatin analog treatment would be appropriate but wherein the subject is not being treated with a compstatin analog for such a disorder or condition or, in some embodiments, if the subject is being treated with a compstatin analog for such a disorder or condition, a different dose, formulation, compstatin analog, and/or route or method of administration, etc., is used.

Complement System

In order to facilitate an understanding of the invention, and without intending to limit the invention in any way, this section provides an overview of complement and its pathways of activation. Further details are found, e.g., in *Kuby Immunology*, 6$^{th}$ ed., 2006; Paul, W. E., *Fundamental Immunology*, Lippincott Williams & Wilkins; 6$^{th}$ ed., 2008; and Walport M J., Complement. First of two parts. *N Engl J Med.*, 344(14): 1058-66, 2001.

Complement is an arm of the innate immune system that plays an important role in defending the body against infectious agents. The complement system comprises more than 30 serum and cellular proteins that are involved in three major pathways, known as the classical, alternative, and lectin pathways. The classical pathway is usually triggered by binding of a complex of antigen and IgM or IgG antibody to C1 (though certain other activators can also initiate the pathway). Activated C1 cleaves C4 and C2 to produce C4a and C4b, in addition to C2a and C2b. C4b and C2a combine to form C3 convertase, which cleaves C3 to form C3a and C3b. Binding of C3b to C3 convertase produces C5 convertase, which cleaves C5 into C5a and C5b. C3a, C4a, and C5a are anaphylotoxins and mediate multiple reactions in the acute inflammatory response. C3a and C5a are also chemotactic factors that attract immune system cells such as neutrophils.

The alternative pathway is initiated by, e.g., microbial surfaces and various complex polysaccharides. In this pathway, C3b, resulting from cleavage of C3, which occurs spontaneously at a low level, binds to targets, e.g., on cell surfaces and forms a complex with factor B, which is later cleaved by factor D, resulting in a C3 convertase. Cleavage of C3 and binding of another molecule of C3b to the C3 convertase gives rise to a C5 convertase. C3 and C5 convertases of this pathway are regulated by CR1, DAF, MCP, and fH. The mode of action of these proteins involves either decay accelerating activity (i.e., ability to dissociate convertases), ability to serve as cofactors in the degradation of C3b or C4b by factor I, or both.

The C5 convertases produced in both pathways cleave C5 to produce C5a and C5b. C5b then binds to C6, C7, and C8 to form C5b-8, which catalyzes polymerization of C9 to form the C5b-9 membrane attack complex (MAC). The MAC inserts itself into target cell membranes and causes cell lysis. Small amounts of MAC on the membrane of cells may have a variety of consequences other than cell death.

The lectin complement pathway is initiated by binding of mannose-binding lectin (MBL) and MBL-associated serine protease (MASP) to carbohydrates. The MB1-1 gene (known as LMAN-1 in humans) encodes a type I integral membrane protein localized in the intermediate region between the endoplasmic reticulum and the Golgi. The MBL-2 gene encodes the soluble mannose-binding protein found in serum. In the human lectin pathway, MASP-1 and MASP-2 are involved in the proteolysis of C4 and C2, leading to a C3 convertase described above.

Complement activity is regulated by various mammalian proteins referred to as complement control proteins (CCPs) or regulators of complement activation (RCA) proteins (U.S. Pat. No. 6,897,290). These proteins differ with respect to ligand specificity and mechanism(s) of complement inhibition. They may accelerate the normal decay of convertases and/or function as cofactors for factor I, to enzymatically cleave C3b and/or C4b into smaller fragments. CCPs are characterized by the presence of multiple (typically 4-56) homologous motifs known as short consensus repeats (SCR), complement control protein (CCP) modules, or SUSHI domains, about 50-70 amino acids in length that contain a conserved motif including four disulfide-bonded cysteines (two disulfide bonds), proline, tryptophan, and many hydrophobic residues. The CCP family includes complement receptor type 1 (CR1; C3b:C4b receptor), complement receptor type 2 (CR2), membrane cofactor protein (MCP; CD46), decay-accelerating factor (DAF), complement factor H (fH), and C4b-binding protein (C4bp). CD59 is a membrane-bound complement regulatory protein unrelated structurally to the CCPs.

Compstatin Analogs

Compstatin is a cyclic peptide that binds to C3 and inhibits complement activation by, e.g., inhibiting cleavage of C3 to C3a and C3b by convertase. U.S. Pat. No. 6,319,897 describes a peptide having the sequence Ile-[Cys-Val-Val-Gln-Asp-Trp-Gly-His-His-Arg-Cys]-Thr (SEQ ID NO: 1), with the disulfide bond between the two cysteines denoted by brackets. It will be understood that the name "compstatin"

was not used in U.S. Pat. No. 6,319,897 but was subsequently adopted in the scientific and patent literature (see, e.g., Morikis, et al., *Protein Sci.*, 7(3):619-27, 1998) to refer to a peptide having the same sequence as SEQ ID NO: 2 disclosed in U.S. Pat. No. 6,319,897, but amidated at the C terminus as shown in Table 1 (SEQ ID NO: 8). The term "compstatin" is used herein consistently with such usage (i.e., to refer to SEQ ID NO: 8). Compstatin analogs that have higher complement inhibiting activity than compstatin have been developed. See, e.g., WO2004/026328 (PCT/US2003/029653), Morikis, D., et al., *Biochem Soc Trans.* 32(Pt 1):28-32, 2004, Mallik, B., et al., *J. Med. Chem.*, 274-286, 2005; Katragadda, M., et al. *J. Med. Chem.*, 49: 4616-4622, 2006; WO2007062249 (PCT/US2006/045539); WO2007044668 (PCT/US2006/039397), WO/2009/046198 (PCT/US2008/078593); WO/2010/127336 (PCT/US2010/033345) and discussion below.

Compstatin analogs may be acetylated or amidated, e.g., at the N-terminus and/or C-terminus. For example, compstatin analogs may be acetylated at the N-terminus and amidated at the C-terminus Consistent with usage in the art, "compstatin" as used herein, and the activities of compstatin analogs described herein relative to that of compstatin, refer to compstatin amidated at the C-terminus (Mallik, 2005, supra).

Concatamers or multimers of compstatin or a complement inhibiting analog thereof are also of use in the present invention.

As used herein, the term "compstatin analog" includes compstatin and any complement inhibiting analog thereof. The term "compstatin analog" encompasses compstatin and other compounds designed or identified based on compstatin and whose complement inhibiting activity is at least 50% as great as that of compstatin as measured, e.g., using any complement activation assay accepted in the art or substantially similar or equivalent assays. Certain suitable assays are described in U.S. Pat. No. 6,319,897, WO2004/026328, Morikis, supra, Mallik, supra, Katragadda 2006, supra, WO2007062249 (PCT/US2006/045539); WO2007044668 (PCT/US2006/039397), WO/2009/046198 (PCT/US2008/078593); and/or WO/2010/127336 (PCT/US2010/033345). The assay may, for example, measure alternative or classical pathway-mediated erythrocyte lysis or be an ELISA assay. In some embodiments, an assay described in WO/2010/135717 (PCT/US2010/035871) is used.

The activity of a compstatin analog may be expressed in terms of its $IC_{50}$ (the concentration of the compound that inhibits complement activation by 50%), with a lower $IC_{50}$ indicating a higher activity as recognized in the art. The activity of a preferred compstatin analog for use in the present invention is at least as great as that of compstatin. It is noted that certain modifications known to reduce or eliminate complement inhibiting activity and may be explicitly excluded from any embodiment of the invention. The $IC_{50}$ of compstatin has been measured as 12 µM using an alternative pathway-mediated erythrocyte lysis assay (WO2004/026328). It will be appreciated that the precise $IC_{50}$ value measured for a given compstatin analog will vary with experimental conditions (e.g., the serum concentration used in the assay). Comparative values, e.g., obtained from experiments in which $IC_{50}$ is determined for multiple different compounds under substantially identical conditions, are of use. In one embodiment, the $IC_{50}$ of the compstatin analog is no more than the $IC_{50}$ of compstatin. In certain embodiments of the invention the activity of the compstatin analog is between 2 and 99 times that of compstatin (i.e., the analog has an $IC_{50}$ that is less than the $IC_{50}$ of compstatin by a factor of between 2 and 99). For example, the activity may be between 10 and 50 times as great as that of compstatin, or between 50 and 99 times as great as that of compstatin. In certain embodiments of the invention the activity of the compstatin analog is between 99 and 264 times that of compstatin. For example, the activity may be 100, 110, 120, 130, 140, 150, 160, 170, 180, 190, 200, 210, 220, 230, 240, 250, 260, or 264 times as great as that of compstatin. In certain embodiments the activity is between 250 and 300, 300 and 350, 350 and 400, or 400 and 500 times as great as that of compstatin. The invention further contemplates compstatin analogs having activities between 500 and 1000 times that of compstatin, or more, e.g., between 1000 and 2000 times that of compstatin, or more. In certain embodiments the $IC_{50}$ of the compstatin analog is between about 0.2 µM and about 0.5 µM. In certain embodiments the $IC_{50}$ of the compstatin analog is between about 0.1 µM and about 0.2 µM. In certain embodiments the $IC_{50}$ of the compstatin analog is between about 0.05 µM and about 0.1 µM. In certain embodiments the $IC_{50}$ of the compstatin analog is between about 0.001 µM and about 0.05 µM.

The $K_d$ of compstatin binding to C3 can be measured using isothermal titration calorimetry (Katragadda, et al., *J. Biol. Chem.*, 279(53), 54987-54995, 2004). Binding affinity of a variety of compstatin analogs for C3 has been correlated with their activity, with a lower $K_d$ indicating a higher binding affinity, as recognized in the art. A linear correlation between binding affinity and activity was shown for certain analogs tested (Katragadda, 2004, supra; Katragadda 2006, supra). In certain embodiments of the invention the compstatin analog binds to C3 with a $K_d$ of between 0.1 µM and 1.0 µM, between 0.05 µM and 0.1 µM, between 0.025 µM and 0.05 µM, between 0.015 µM and 0.025 µM, between 0.01 µM and 0.015 µM, or between 0.001 µM and 0.01 µM.

Compounds "designed or identified based on compstatin" include, but are not limited to, compounds that comprise an amino acid chain whose sequence is obtained by (i) modifying the sequence of compstatin (e.g., replacing one or more amino acids of the sequence of compstatin with a different amino acid or amino acid analog, inserting one or more amino acids or amino acid analogs into the sequence of compstatin, or deleting one or more amino acids from the sequence of compstatin); (ii) selection from a phage display peptide library in which one or more amino acids of compstatin is randomized, and optionally further modified according to method (i); or (iii) identified by screening for compounds that compete with compstatin or any analog thereof obtained by methods (i) or (ii) for binding to C3 or a fragment thereof. Many useful compstatin analogs comprise a hydrophobic cluster, a β-turn, and a disulfide bridge.

In certain embodiments of the invention the sequence of the compstatin analog comprises or consists essentially of a sequence that is obtained by making 1, 2, 3, or 4 substitutions in the sequence of compstatin, i.e., 1, 2, 3, or 4 amino acids in the sequence of compstatin is replaced by a different standard amino acid or by a non-standard amino acid. In certain embodiments of the invention the amino acid at position 4 is altered. In certain embodiments of the invention the amino acid at position 9 is altered. In certain embodiments of the invention the amino acids at positions 4 and 9 are altered. In certain embodiments of the invention only the amino acids at positions 4 and 9 are altered. In certain embodiments of the invention the amino acid at position 4 or 9 is altered, or in certain embodiments both amino acids 4 and 9 are altered, and in addition up to 2 amino acids located at positions selected from 1, 7, 10, 11, and 13 are altered. In certain embodiments of the invention the amino acids at positions 4, 7, and 9 are altered. In certain embodiments of the invention amino acids at position 2, 12, or both are altered, provided that the alteration preserves the ability of the compound to cyclized. Such alteration(s) at positions 2 and/or 12 may be in addition to the alteration(s) at position 1, 4, 7, 9, 10, 11, and/or 13. Optionally the sequence of any of the compstatin analogs whose sequence is obtained by replacing one or more amino acids of compstatin sequence further includes up to 1, 2, or 3 additional amino acids at the C-terminus. In one embodiment, the additional amino acid is Gly. Optionally the sequence of any of the compstatin analogs whose sequence is obtained by replacing one or more amino acids of compstatin sequence further includes up to 5, or up to 10 additional amino acids at the C-terminus. It should be understood that compstatin analogs may have any one or more of the characteristics or features of the various embodiments described herein, and characteristics or features of any embodiment may additionally characterize any other embodiment described herein, unless otherwise stated or evident from the context. In certain embodiments of the invention the sequence of the compstatin analog comprises or consists essentially of a sequence identical to that of compstatin except at positions corresponding to positions 4 and 9 in the sequence of compstatin.

Compstatin and certain compstatin analogs having somewhat greater activity than compstatin contain only standard amino acids ("standard amino acids" are glycine, leucine, isoleucine, valine, alanine, phenylalanine, tyrosine, tryptophan, aspartic acid, asparagine, glutamic acid, glutamine, cysteine, methionine, arginine, lysine, proline, serine, threonine and histidine). Certain compstatin analogs having improved activity incorporate one or more non-standard amino acids. Useful non-standard amino acids include singly and multiply halogenated (e.g., fluorinated) amino acids, D-amino acids, homo-amino acids, N-alkyl amino acids, dehydroamino acids, aromatic amino acids (other than phenylalanine, tyrosine and tryptophan), ortho-, meta- or para-aminobenzoic acid, phospho-amino acids, methoxylated amino acids, and α,α-disubstituted amino acids. In certain embodiments of the invention, a compstatin analog is designed by replacing one or more L-amino acids in a compstatin analog described elsewhere herein with the corresponding D-amino acid. Such compounds and methods of use thereof are an aspect of the invention. Exemplary non-standard amino acids of use include 2-naphthylalanine (2-NaI), 1-naphthylalanine (1-NaI), 2-indanylglycine carboxylic acid (2Ig1), dihydrotrpyophan (Dht), 4-benzoyl-L-phenylalanine (Bpa), 2-α-aminobutyric acid (2-Abu), 3-α-aminobutyric acid (3-Abu), 4-α-aminobutyric acid (4-Abu), cyclohexylalanine (Cha), homocyclohexylalanine (hCha), 4-fluoro-L-tryptophan (4fW), 5-fluoro-L-tryptophan (5fW), 6-fluoro-L-tryptophan (6fW), 4-hydroxy-L-tryptophan (4OH-W), 5-hydroxy-L-tryptophan (5OH-W), 6-hydroxy-L-tryptophan (6OH-W), 1-methyl-L-tryptophan (1MeW), 4-methyl-L-tryptophan (4MeW), 5-methyl-L-tryptophan (5MeW), 7-aza-L-tryptophan (7aW), α-methyl-L-tryptophan (αMeW), β-methyl-L-tryptophan (βMeW), N-methyl-L-tryptophan (NMeW), ornithine (orn), citrulline, norleucine, γ-glutamic acid, etc.

In certain embodiments of the invention the compstatin analog comprises one or more Trp analogs (e.g., at position 4 and/or 7 relative to the sequence of compstatin). Exemplary Trp analogs are mentioned above. See also Beene, et. al. *Biochemistry* 41: 10262-10269, 2002 (describing, inter alia, singly- and multiply-halogenated Trp analogs); Babitzke & Yanofsky, *J. Biol. Chem.* 270: 12452-12456, 1995 (describing, inter alia, methylated and halogenated Trp and other Trp and indole analogs); and U.S. Pat. Nos. 6,214,790, 6,169,057, 5,776,970, 4,870,097, 4,576,750 and 4,299,838. Other Trp analogs include variants that are substituted (e.g., by a methyl group) at the α or β carbon and, optionally, also at one or more positions of the indole ring Amino acids comprising two or more aromatic rings, including substituted, unsubstituted, or alternatively substituted variants thereof, are of interest as Trp analogs. In certain embodiments of the invention the Trp analog, e.g., at position 4, is 5-methoxy, 5-methyl-, 1-methyl-, or 1-formyl-tryptophan. In certain embodiments of the invention a Trp analog (e.g., at position 4) comprising a 1-alkyl substituent, e.g., a lower alkyl (e.g., $C_1$-$C_5$) substituent is used. In certain embodiments, $N(\alpha)$ methyl tryptophan or 5-methyltryptophan is used. In some embodiments, an analog comprising a 1-alkanyol substituent, e.g., a lower alkanoyl (e.g., $C_1$-$C_5$) is used. Examples include 1-acetyl-L-tryptophan and L-β-tryptophan.

In certain embodiments the Trp analog has increased hydrophobic character relative to Trp. For example, the indole ring may be substituted by one or more alkyl (e.g., methyl) groups. In certain embodiments the Trp analog participates in a hydrophobic interaction with C3. Such a Trp analog may be located, e.g., at position 4 relative to the sequence of compstatin. In certain embodiments the Trp analog comprises a substituted or unsubstituted bicyclic aromatic ring component or two or more substituted or unsubstituted monocyclic aromatic ring components.

In certain embodiments the Trp analog has increased propensity to form hydrogen bonds with C3 relative to Trp but does not have increased hydrophobic character relative to Trp. The Trp analog may have increased polarity relative to Trp and/or an increased ability to participate in an electrostatic interaction with a hydrogen bond donor on C3. Certain exemplary Trp analogs with an increased hydrogen bond forming character comprise an electronegative substituent on the indole ring. Such a Trp analog may be located, e.g., at position 7 relative to the sequence of compstatin.

In certain embodiments of the invention the compstatin analog comprises one or more Ala analogs (e.g., at position 9 relative to the sequence of compstatin), e.g., Ala analogs that are identical to Ala except that they include one or more $CH_2$ groups in the side chain. In certain embodiments the Ala analog is an unbranched single methyl amino acid such as 2-Abu. In certain embodiments of the invention the compstatin analog comprises one or more Trp analogs (e.g., at position 4 and/or 7 relative to the sequence of compstatin) and an Ala analog (e.g., at position 9 relative to the sequence of compstatin).

In certain embodiments of the invention the compstatin analog is a compound that comprises a peptide that has a sequence of (X'aa)$_n$-Gln-Asp-Xaa-Gly-(X"aa)$_m$, (SEQ ID NO: 2) wherein each X'aa and each X"aa is an independently selected amino acid or amino acid analog, wherein Xaa is Trp or an analog of Trp, and wherein n>1 and m>1 and n+m is between 5 and 21. The peptide has a core sequence of Gln-Asp-Xaa-Gly, where Xaa is Trp or an analog of Trp, e.g., an analog of Trp having increased propensity to form hydrogen bonds with an H-bond donor relative to Trp but, in certain embodiments, not having increased hydrophobic character relative to Trp. For example, the analog may be one in which the indole ring of Trp is substituted with an electronegative moiety, e.g., a halogen such as fluorine. In one embodiment Xaa is 5-fluorotryptophan. Absent evidence to the contrary, one of skill in the art would recognize that any non-naturally occurring peptide whose sequence comprises this core sequence and that inhibits complement activation and/or binds to C3 will have been designed based on the sequence of compstatin. In an alternative embodiment Xaa is an amino acid or amino acid analog other than a Trp analog that allows the Gln-Asp-Xaa-Gly peptide to form a β-turn.

In certain embodiments of the invention the peptide has a core sequence of X'aa-Gln-Asp-Xaa-Gly (SEQ ID NO: 3), where X'aa and Xaa are selected from Trp and analogs of Trp. In certain embodiments of the invention the peptide has a core sequence of X'aa-Gln-Asp-Xaa-Gly (SEQ ID NO: 3), where X'aa and Xaa are selected from Trp, analogs of Trp, and other amino acids or amino acid analogs comprising at least one aromatic ring. In certain embodiments of the invention the core sequence forms a β-turn in the context of the peptide. The β-turn may be flexible, allowing the peptide to assume two or more conformations as assessed for example, using nuclear magnetic resonance (NMR). In certain embodiments X'aa is an analog of Trp that comprises a substituted or unsubstituted bicyclic aromatic ring component or two or more substituted or unsubstituted monocyclic aromatic ring components. In certain embodiments of the invention X'aa is selected from the group consisting of 2-napthylalanine, 1-napthylalanine, 2-indanylglycine carboxylic acid, dihydrotryptophan, and benzoylphenylalanine. In certain embodiments of the invention X'aa is an analog of Trp that has increased hydrophobic character relative to Trp. For example, X'aa may be 1-methyltryptophan. In certain embodiments of the invention Xaa is an analog of Trp that has increased propensity to form hydrogen bonds relative to Trp but, in certain embodiments, not having increased hydrophobic character relative to Trp. In certain embodiments of the invention the analog of Trp that has increased propensity to form hydrogen bonds relative to Trp comprises a modification on the indole ring of Trp, e.g., at position 5, such as a substitution of a halogen atom for an H atom at position 5. For example, Xaa may be 5-fluorotryptophan.

In certain embodiments of the invention the peptide has a core sequence of X'aa-Gln-Asp-Xaa-Gly-X"aa (SEQ ID NO: 4), where X'aa and Xaa are each independently selected from Trp and analogs of Trp and X"aa is selected from His, Ala, analogs of Ala, Phe, and Trp. In certain embodiments of the invention X'aa is an analog of Trp that has increased hydrophobic character relative to Trp, such as 1-methyltryptophan or another Trp analog having an alkyl substituent on the indole ring (e.g., at position 1, 4, 5, or 6). In certain embodiments X'aa is an analog of Trp that comprises a substituted or unsubstituted bicyclic aromatic ring component or two or more substituted or unsubstituted monocyclic aromatic ring components. In certain embodiments of the invention X'aa is selected from the group consisting of 2-napthylalanine, 1-napthylalanine, 2-indanylglycine carboxylic acid, dihydrotryptophan, and benzoylphenylalanine. In certain embodiments of the invention Xaa is an analog of Trp that has increased propensity to form hydrogen bonds with C3 relative to Trp but, in certain embodiments, not having increased hydrophobic character relative to Trp. In certain embodiments of the invention the analog of Trp that has increased propensity to form hydrogen bonds relative to Trp comprises a modification on the indole ring of Trp, e.g., at position 5, such as a substitution of a halogen atom for an H atom at position 5. For example, Xaa may be 5-fluorotryptophan. In certain embodiments X"aa is Ala or an analog of Ala such as Abu or another unbranched single methyl amino acid. In certain embodiments of the invention the peptide has a core sequence of X'aa-Gln-Asp-Xaa-Gly-X"aa (SEQ ID NO: 4), where X'aa and Xaa are each independently selected from Trp, analogs of Trp, and amino acids or amino acid analogs comprising at least one aromatic side chain, and X"aa is selected from His, Ala, analogs of Ala, Phe, and Trp. In certain embodiments X"aa is selected from analogs of Trp, aromatic amino acids, and aromatic amino acid analogs.

In certain preferred embodiments of the invention the peptide is cyclic. The peptide may be cyclized via a bond between any two amino acids, one of which is $(X'aa)_n$ and the other of which is located within $(X"aa)_m$. In certain embodiments the cyclic portion of the peptide is between 9 and 15 amino acids in length, e.g., 10-12 amino acids in length. In certain embodiments the cyclic portion of the peptide is 11 amino acids in length, with a bond (e.g., a disulfide bond) between amino acids at positions 2 and 12. For example, the peptide may be 13 amino acids long, with a bond between amino acids at positions 2 and 12 resulting in a cyclic portion 11 amino acids in length.

In certain embodiments the peptide comprises or consists of the sequence X'aa1-X'aa2-X'aa3-X'aa4-Gln-Asp-Xaa-Gly-X"aa1-X"aa2-X"aa3-X"aa4-X"aa5 (SEQ ID NO: 5). In certain embodiments X'aa4 and Xaa are selected from Trp and analogs of Trp, and X'aa1, X'aa2, X'aa3, X"aa1, X"aa2, X"aa3, X"aa4, and X"aa5 are independently selected from among amino acids and amino acid analogs. In certain embodiments X'aa4 and Xaa are selected from aromatic amino acids and aromatic amino acid analogs. Any one or more of X'aa1, X'aa2, X'aa3, X"aa1, X"aa2, X"aa3, X"aa4, and X"aa5 may be identical to the amino acid at the corresponding position in compstatin. In one embodiment, X"aa1 is Ala or a single methyl unbranched amino acid. The peptide may be cyclized via a covalent bond between (i) X'aa1, X'aa2, or X'aa3; and (ii) X"aa2, X"aa3, X"aa4 or X"aa5. In one embodiment the peptide is cyclized via a covalent bond between X'aa2 and X"aa4. In one embodiment the covalently bound amino acid are each Cys and the covalent bond is a disulfide (S—S) bond. In other embodiments the covalent bond is a C—C, C—O, C—S, or C—N bond. In certain embodiments one of the covalently bound residues is an amino acid or amino acid analog having a side chain that comprises a primary or secondary amine, the other covalently bound residue is an amino acid or amino acid analog having a side chain that comprises a carboxylic acid group, and the covalent bond is an amide bond. Amino acids or amino acid analogs having a side chain that comprises a primary or secondary amine include lysine and diaminocarboxylic acids of general structure $NH_2(CH_2)_nCH(NH_2)COOH$ such as 2,3-diaminopropionic acid (dapa), 2,4-diaminobutyric acid (daba), and ornithine (orn), wherein n=1 (dapa), 2 (daba), and 3 (orn), respectively. Examples of amino acids having a side chain that comprises a carboxylic acid group include dicarboxylic amino acids such as glutamic acid and aspartic acid. Analogs such as beta-hydroxy-L-glutamic acid may also be used.

In certain embodiments, the compstatin analog is a compound that comprises a peptide having a sequence:
Xaa1-Cys-Val-Xaa2-Gln-Asp-Xaa2*-Gly-Xaa3-His-Arg-Cys-Xaa4 (SEQ ID NO: 6); wherein:
Xaa1 is Ile, Val, Leu, $B^1$-Ile, $B^1$-Val, $B^1$-Leu or a dipeptide comprising Gly-Ile or $B^1$-Gly-Ile, and $B^1$ represents a first blocking moiety;
Xaa2 and Xaa2* are independently selected from Trp and analogs of Trp;
Xaa3 is His, Ala or an analog of Ala, Phe, Trp, or an analog of Trp;
Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of the L-Thr, D-Thr, Ile, Val, Gly, Ala, or Asn optionally is replaced by a second blocking moiety $B^2$; and the two Cys residues are joined by a disulfide bond. In some embodiments, Xaa4 is Leu, Nle, His, or Phe or a dipeptide selected from Xaa5-Ala and Xaa5-Asn, or a tripeptide Xaa5-Ala-Asn, wherein Xaa5 is selected from Leu, Nle, His or Phe, and wherein a carboxy terminal —OH of any of the L-Thr, D-Thr, Ile, Val, Gly, Leu, Nle, His, Phe, Ala, or Asn optionally is replaced by a second blocking moiety $B^2$; and the two Cys residues are joined by a disulfide bond.

In other embodiments Xaa1 is absent or is any amino acid or amino acid analog, and Xaa2, Xaa2*, Xaa3, and Xaa4 are as defined above. If Xaa1 is absent, the N-terminal Cys residue may have a blocking moiety $B^1$ attached thereto.

In another embodiment, Xaa4 is any amino acid or amino acid analog and Xaa1, Xaa2, Xaa2*, and Xaa3 are as defined above. In another embodiment Xaa4 is a dipeptide selected from the group consisting of: Thr-Ala and Thr-Asn, wherein the carboxy terminal —OH or the Ala or Asn is optionally replaced by a second blocking moiety $B^2$.

In any of the embodiments of the compstatin analog of SEQ ID NO: 6, Xaa2 may be Trp.

In any of the embodiments of the compstatin analog of SEQ ID NO: 6, Xaa2 may be an analog of Trp comprising a substituted or unsubstituted bicyclic aromatic ring component or two or more substituted or unsubstituted monocyclic aromatic ring components. For example, the analog of Trp may be selected from 2-naphthylalanine (2-Nal), 1-naphthylalanine (1-Nal), 2-indanylglycine carboxylic acid (Igl), dihydrotrpytophan (Dht), and 4-benzoyl-L-phenylalanine.

In any of the embodiments of the compstatin analog of SEQ ID NO: 6, Xaa2 may be an analog of Trp having increased hydrophobic character relative to Trp. For example, the analog of Trp may be selected from 1-methyltryptophan, 4-methyltryptophan, 5-methyltryptophan, and 6-methyltryptophan. In one embodiment, the analog of Trp is 1-methyltryptophan. In one embodiment, Xaa2 is 1-methyltryptophan, Xaa2* is Trp, Xaa3 is Ala, and the other amino acids are identical to those of compstatin.

In any of the embodiments of the compstatin analog of SEQ ID NO: 6, Xaa2* may be an analog of Trp such as an analog of Trp having increased hydrogen bond forming propensity with C3 relative to Trp, which, in certain embodiments, does not have increased hydrophobic character relative to Trp. In certain embodiments the analog of Trp comprises an electronegative substituent on the indole ring. For example, the analog of Trp may be selected from 5-fluorotryptophan and 6-fluorotryptophan.

In certain embodiments of the invention Xaa2 is Trp and Xaa2* is an analog of Trp having increased hydrogen bond forming propensity with C3 relative to Trp which, in certain embodiments, does not have increased hydrophobic character relative to Trp. In certain embodiments of the compstatin analog of SEQ ID NO: 6, Xaa2 is analog of Trp having increased hydrophobic character relative to Trp such as an analog of Trp selected from 1-methyltryptophan, 4-methyltryptophan, 5-methyltryptophan, and 6-methyltryptophan, and Xaa2* is an analog of Trp having increased hydrogen bond forming propensity with C3 relative to Trp which, in certain embodiments, does not have increased hydrophobic character relative to Trp. For example, in one embodiment Xaa2 is methyltryptophan and Xaa2* is 5-fluorotryptophan.

In certain of the afore-mentioned embodiments, Xaa3 is Ala. In certain of the afore-mentioned embodiments Xaa3 is a single methyl unbranched amino acid, e.g., Abu.

The invention further provides compstatin analogs of SEQ ID NO: 6, as described above, wherein Xaa2 and Xaa2* are independently selected from Trp, analogs of Trp, and other amino acids or amino acid analogs that comprise at least one aromatic ring, and Xaa3 is His, Ala or an analog of Ala, Phe, Trp, an analog of Trp, or another aromatic amino acid or aromatic amino acid analog.

In certain embodiments of the invention the blocking moiety present at the N- or C-terminus of any of the compstatin analogs described herein is any moiety that stabilizes a peptide against degradation that would otherwise occur in mammalian (e.g., human or non-human primate) blood or interstitial fluid. For example, blocking moiety $B^1$ could be any moiety that alters the structure of the N-terminus of a peptide so as to inhibit cleavage of a peptide bond between the N-terminal amino acid of the peptide and the adjacent amino acid. Blocking moiety $B^2$ could be any moiety that alters the structure of the C-terminus of a peptide so as to inhibit cleavage of a peptide bond between the C-terminal amino acid of the peptide and the adjacent amino acid. Any suitable blocking moieties known in the art could be used. In certain embodiments of the invention blocking moiety $B^1$ comprises an acyl group (i.e., the portion of a carboxylic acid that remains following removal of the —OH group). The acyl group typically comprises between 1 and 12 carbons, e.g., between 1 and 6 carbons. For example, in certain embodiments of the invention blocking moiety $B^1$ is selected from the group consisting of: formyl, acetyl, proprionyl, butyryl, isobutyryl, valeryl, isovaleryl, etc. In one embodiment, the blocking moiety $B^1$ is an acetyl group, i.e., Xaa1 is Ac-Ile, Ac-Val, Ac-Leu, or Ac-Gly-Ile.

In certain embodiments of the invention blocking moiety $B^2$ is a primary or secondary amine (—NH$_2$ or —NHR$^1$, wherein R is an organic moiety such as an alkyl group).

In certain embodiments of the invention blocking moiety $B^1$ is any moiety that neutralizes or reduces the negative charge that may otherwise be present at the N-terminus at physiological pH. In certain embodiments of the invention blocking moiety $B^2$ is any moiety that neutralizes or reduces the negative charge that may otherwise be present at the C-terminus at physiological pH.

In certain embodiments of the invention, the compstatin analog is acetylated or amidated at the N-terminus and/or C-terminus, respectively. A compstatin analog may be acetylated at the N-terminus, amidated at the C-terminus, and or both acetylated at the N-terminus and amidated at the C-terminus. In certain embodiments of the invention a compstatin analog comprises an alkyl or aryl group at the N-terminus rather than an acetyl group.

In certain embodiments, the compstatin analog is a compound that comprises a peptide having a sequence:
Xaa1-Cys-Val-Xaa2-Gln-Asp-Xaa2*-Gly-Xaa3-His-Arg-Cys-Xaa4 (SEQ ID NO: 7); wherein:
Xaa1 is Ile, Val, Leu, Ac-Ile, Ac-Val, Ac-Leu or a dipeptide comprising Gly-Ile or Ac-Gly-Ile;
Xaa2 and Xaa2* are independently selected from Trp and analogs of Trp;
Xaa3 is His, Ala or an analog of Ala, Phe, Trp, or an analog of Trp;
Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of L-Thr, D-Thr, Ile, Val, Gly, Ala, or Asn optionally is replaced by —NH$_2$; and the two Cys residues are joined by a disulfide bond. In some embodiments, Xaa4 is Leu, Nle, His, or Phe or a depeptide selected from Xaa5-Ala and Xaa5-Asn, or a tripeptide Xaa5-Ala-Asn, wherein Xaa5 is selected from Leu, Nle, His or Phe, and wherein a carboxy terminal —OH of any of the L-Thr, D-Thr, Ile, Val, Gly, Leu, Nle, His, Phe, Ala, or Asn optionally is replaced by a second blocking moiety B2; and the two Cys residues are joined by a disulfide bond.
In some embodiments, Xaa1, Xaa2, Xaa2*, Xaa3, and Xaa4 are as described above for the various embodiments of SEQ ID NO: 6. For example, in certain embodiments Xaa2* is Trp.

In certain embodiments Xaa2 is an analog of Trp having increased hydrophobic character relative to Trp, e.g., 1-methyltryptophan. In certain embodiments Xaa3 is Ala. In certain embodiments Xaa3 is a single methyl unbranched amino acid.

In certain embodiments of the invention Xaa1 is Ile and Xaa4 is L-Thr.

In certain embodiments of the invention Xaa1 is Ile, Xaa2* is Trp, and Xaa4 is L-Thr.

The invention further provides compstatin analogs of SEQ ID NO: 7, as described above, wherein Xaa2 and Xaa2* are independently selected from Trp, analogs of Trp, other amino acids or aromatic amino acid analogs, and Xaa3 is His, Ala or an analog of Ala, Phe, Trp, an analog of Trp, or another aromatic amino acid or aromatic amino acid analog.

In certain embodiments of any of the compstatin analogs described herein, an analog of Phe is used rather than Phe.

Table 1 provides a non-limiting list of compstatin analogs useful in the present invention. The analogs are referred to in abbreviated form in the left column by indicating specific modifications at designated positions (1-13) as compared to the parent peptide, compstatin. Consistent with usage in the art, "compstatin" as used herein, and the activities of compstatin analogs described herein relative to that of compstatin, refer to the compstatin peptide amidated at the C-terminus. Unless otherwise indicated, peptides in Table 1 are amidated at the C-terminus. Bold text is used to indicate certain modifications. Activity relative to compstatin is based on published data and assays described therein (WO2004/026328, WO2007044668, Mallik, 2005; Katragadda, 2006). Where multiple publications reporting an activity were consulted, the more recently published value is used, and it will be recognized that values may be adjusted in the case of differences between assays. It will also be appreciated that in certain embodiments of the invention the peptides listed in Table 1 are cyclized via a disulfide bond between the two Cys residues when used in the therapeutic compositions and methods of the invention. Alternate means for cyclizing the peptides are also within the scope of the invention. As noted above, in various embodiments of the invention one or more amino acid(s) of a compstatin analog (e.g., any of the compstatin analogs disclosed herein) can be an N-alkyl amino acid (e.g., an N-methyl amino acid). For example, and without limitation, at least one amino acid within the cyclic portion of the peptide, at least one amino acid N-terminal to the cyclic portion, and/or at least one amino acid C-terminal to the cyclic portion may be an N-alkyl amino acid, e.g., an N-methyl amino acid. In some embodiments of the invention, for example, a compstatin analog comprises an N-methyl glycine, e.g., at the position corresponding to position 8 of compstatin and/or at the position corresponding to position 13 of compstatin. In some embodiments, one or more of the compstatin analogs in Table 1 contains at least one N-methyl glycine, e.g., at the position corresponding to position 8 of compstatin and/or at the position corresponding to position 13 of compstatin.

TABLE 1

| Peptide | Sequence | SEQ ID NO: | Activity over compstatin |
|---|---|---|---|
| Compstatin | H-ICVVQDWGHHRCT-CONH2 | 8 | * |
| Ac-compstatin | Ac-ICVVQDWGHHRCT-CONH2 | 9 | 3xmore |
| Ac-V4Y/H9A | Ac-ICVYQDWGAHRCT-CONH2 | 10 | 14xmore |
| Ac-V4W/H9A-OH | Ac-ICVWQDWGAHRCT-COOH | 11 | 27xmore |
| Ac-V4W/H9A | Ac-ICVWQDWGAHRCT-CONH2 | 12 | 45xmore |
| Ac-V4W/H9A/T13dT-OH | Ac-ICVWQDWGAHRCdT-COOH | 13 | 55xmore |
| Ac-V4(2-Nal)/H9A | Ac-ICV(2-Nal)QDWGAHRCT-CONH2 | 14 | 99xmore |
| Ac V4(2-Nal)/H9A-OH | Ac-ICV(2-Nal)QDWGAHRCT-COOH | 15 | 38xmore |
| Ac V4(1-Nal)/H9A-OH | Ac-ICV(1-Nal)QDWGAHRCT-COOH | 16 | 30xmore |
| Ac-V42Ig1/H9A | Ac-ICV(2-Ig1)QDWGAHRCT-CONH2 | 17 | 39xmore |
| Ac-V42Ig1/H9A-OH | Ac-ICV(2-Ig1)QDWGAHRCT-COOH | 18 | 37xmore |
| Ac-V4Dht/H9A-OH | Ac-ICVDhtQDWGAHRCT-COOH | 19 | 5xmore |
| Ac-V4(Bpa)/H9A-OH | Ac-ICV(Bpa)QDWGAHRCT-COOH | 20 | 49xmore |
| Ac-V4(Bpa)/H9A | Ac-ICV(Bpa)QDWGAHRCT-CONH2 | 21 | 86xmore |
| Ac-V4(Bta)/H9A-OH | Ac-ICV(Bta)QDWGAHRCT-COOH | 22 | 65xmore |
| Ac-V4(Bta)/H9A | Ac-ICV(Bta)QDWGAHRCT-CONH2 | 23 | 64xmore |
| Ac-V4W/H9(2-Abu) | Ac-ICVWQDWG(2-Abu)HRCT-CONH2 | 24 | 64xmore |
| +GN4W/H9A +AN-OH | H-GICVWQDWGAHRCTAN-COOH | 25 | 38xmore |
| Ac-V4(5fW)/H9A | Ac-ICV(5fW)QDWGAHRCT-CONH$_2$ | 26 | 31xmore |
| Ac-V4(5-MeW)/H9A | Ac-ICV(5-methyl-W)QDWGAHRCT-CONH$_2$ | 27 | 67xmore |
| Ac-V4(1-MeW)/H9A | Ac-ICV(1-methyl-W)QDWGAHRCT-CONH$_2$ | 28 | 264xmore |

TABLE 1-continued

| Peptide | Sequence | SEQ ID NO: | Activity over compstatin |
|---|---|---|---|
| Ac-V4W/W7(5fW)/H9A | Ac-ICVWQD(5fW)G<u>A</u>HRCT-coNH$_2$ | 29 | 121xmore |
| Ac-V4(5fW)/W7(5fW)/H9A | Ac-ICV(5fW)QD(5fW)G<u>A</u>HRCT-CONH$_2$ | 30 | NA |
| Ac-V4(5-MeW)/W7(5fW)H9A | Ac-ICV(5-methyl-W)QD(5fW)G<u>A</u>HRCT-CONH$_2$ | 31 | NA |
| Ac-V4(1MeW)/W7(5fW)/H9A | Ac-ICV(1-methyl-W)QD(5fW)G<u>A</u>HRCT-CONH$_2$ | 32 | 264xmore |
| +G/V4(6fW)/W7(6fW)H9A+N-OH | H-GICV(6fW)QD(6fW)G<u>A</u>HRCT<u>N</u>-COOH | 33 | 126xmore |
| Ac-V4(1-formyl-W)/H9A | Ac-ICV(1-formyl-W)QDWG<u>A</u>HRCT-CONH$_2$ | 34 | 264xmore |
| Ac-V4(5-methoxy-W)/H9A | Ac-ICV(1-methyoxy-W)QDWG<u>A</u>HRCT-CONH$_2$ | 35 | 76xmore |
| G/V4(5f-W)/W7(5fW)/H9A+N-OH | H-GICV(5fW)QD(5fW)G<u>A</u>HRCT<u>N</u>-COOH | 36 | 112xmore |

NA = not available

In certain embodiments of the compositions and methods of the invention the compstatin analog has a sequence selected from sequences 9-36. In certain embodiments of the compositions and methods of the invention the compstatin analog has a sequence selected from SEQ ID NOs: 14, 21, 28, 29, 32, 33, 34, and 36. In certain embodiments of the compositions and/or methods of the invention the compstatin analog has a sequence selected from SEQ ID NOs: 30 and 31. In one embodiment of the compositions and methods of the invention the compstatin analog has a sequence of SEQ ID NO: 28. In one embodiment of the compositions and methods of the invention the compstatin analog has a sequence of SEQ ID NO: 32. In one embodiment of the compositions and methods of the invention the compstatin analog has a sequence of SEQ ID NO: 34. In one embodiment of the compositions and methods of the invention the compstatin analog has a sequence of SEQ ID NO: 36.

In certain embodiments of the compositions and methods of the invention the compstatin analog has a sequence as set forth in Table 1, but where the Ac— group is replaced by an alternate blocking moiety B$^1$, as described above. In some embodiments the —NH$_2$ group is replaced by an alternate blocking moiety B$^2$, as described above.

In one embodiment, the compstatin analog binds to substantially the same region of the β chain of human C3 as does compstatin. In one embodiment the compstatin analog is a compound that binds to a fragment of the C-terminal portion of the β chain of human C3 having a molecular weight of about 40 kDa to which compstatin binds (Soulika, A. M., et al., *Mol. Immunol.*, 35:160, 1998; Soulika, A. M., et al., *Mol. Immunol.* 43(12):2023-9, 2006). In certain embodiments the compstatin analog is a compound that binds to the binding site of compstatin as determined in a compstatin-C3 structure, e.g., a crystal structure or NMR-derived 3D structure. In certain embodiments the compstatin analog is a compound that could substitute for compstatin in a compstatin-C3 structure and would form substantially the same intermolecular contacts with C3 as compstatin. In certain embodiments the compstatin analog is a compound that binds to the binding site of a peptide having a sequence set forth in Table 1, e.g., SEQ ID NO: 14, 21, 28, 29, 32, 33, 34, or 36 in a peptide-C3 structure, e.g., a crystal structure. In certain embodiments the compstatin analog is a compound that binds to the binding site of a peptide having SEQ ID NO: 30 or 31 in a peptide-C3 structure, e.g., a crystal structure. In certain embodiments the compstatin analog is a compound that could substitute for the peptide of SEQ ID NO: 9-36, e.g., a compound that could substitute for the peptide of SEQ ID NO: 14, 21, 28, 29, 32, 33, 34, or 36 in a peptide-C3 structure and would form substantially the same intermolecular contacts with C3 as the peptide. In certain embodiments the compstatin analog is a compound that could substitute for the peptide of SEQ ID NO: 30 or 31 in a peptide-C3 structure and would form substantially the same intermolecular contacts with C3 as the peptide.

One of ordinary skill in the art will readily be able to determine whether a compstatin analog binds to a fragment of the C-terminal portion of the β chain of C3 using routine experimental methods. For example, one of skill in the art could synthesize a photocrosslinkable version of the compstatin analog by including a photo-crosslinking amino acid such as p-benzoyl-L-phenylalanine (Bpa) in the compound, e.g., at the C-terminus of the sequence (Soulika, A. M., et al, supra). Optionally additional amino acids, e.g., an epitope tag such as a FLAG tag or an HA tag could be included to facilitate detection of the compound, e.g., by Western blotting. The compstatin analog is incubated with the fragment and crosslinking is initiated. Colocalization of the compstatin analog and the C3 fragment indicates binding. Surface plasmon resonance may also be used to determine whether a compstatin analog binds to the compstatin binding site on C3 or a fragment thereof and/or to measure binding affinity. A competition experiment, e.g., wherein binding of a compstatin analog to the compstatin binding site on C3 or a fragment thereof interferes with binding of compstatin, may be used. One of skill in the art would be able to use molecular modeling software programs to predict whether a compound would form substantially the same intermolecular contacts with C3 as would compstatin or a peptide having the sequence of any of the peptides in Table 1, e.g., SEQ ID NO: 14, 21, 28, 29, 32, 33, 34, or 36, or in some embodiments SEQ ID NO: 30 or 31.

Compstatin analogs may be prepared by various synthetic methods of peptide synthesis known in the art via condensation of amino acid residues, e.g., in accordance with conventional peptide synthesis methods, may be prepared by expression in vitro or in living cells from appropriate nucleic acid sequences encoding them using methods known in the art. For example, peptides may be synthesized using standard solid-phase methodologies as described in Malik, supra, Katragadda, supra, WO2004026328, and/or WO2007062249. Potentially reactive moieties such as amino and carboxyl groups, reactive functional groups, etc., may be protected and subsequently deprotected using various protecting groups and methodologies known in the art. See, e.g., "Protective Groups in Organic Synthesis", $3^{rd}$ ed. Greene, T. W. and Wuts, P. G., Eds., John Wiley & Sons, New York: 1999. Peptides may be purified using standard approaches such as reversed-phase HPLC. Separation of diasteriomeric peptides, if desired, may be performed using known methods such as reversed-phase HPLC. Preparations may be lyophilized, if desired, and subsequently dissolved in a suitable solvent, e.g., water. The pH of the resulting solution may be adjusted, e.g. to physiological pH, using a base such as NaOH. Peptide preparations may be characterized by mass spectrometry if desired, e.g., to confirm mass and/or disulfide bond formation. See, e.g., Mallik, 2005, and Katragadda, 2006.

A compstatin analog can be modified by addition of a molecule such as polyethylene glycol (PEG) or similar molecules to stabilize the compound, reduce its immunogenicity, increase its lifetime in the body, increase or decrease its solubility, and/or increase its resistance to degradation. Methods for pegylation are well known in the art (Veronese, F. M. & Harris, Adv. Drug Deliv. Rev. 54, 453-456, 2002; Davis, F. F., Adv. Drug Deliv. Rev. 54, 457-458, 2002); Hinds, K. D. & Kim, S. W. *Adv. Drug Deliv. Rev.* 54, 505-530 (2002; Roberts, M. J., Bentley, M. D. & Harris, J. M. *Adv. Drug Deliv. Rev.* 54, 459-476; 2002); Wang, Y. S. et al. *Adv. Drug Deliv. Rev.* 54, 547-570, 2002). A wide variety of polymers such as PEGs and modified PEGs, including derivatized PEGs to which polypeptides can conveniently be attached are described in Nektar Advanced Pegylation 2005-2006 Product Catalog, Nektar Therapeutics, San Carlos, Calif., which also provides details of appropriate conjugation procedures. In another embodiment a compstatin analog is fused to the Fc domain of an immunoglobulin or a portion thereof. In some other embodiments a compstatin analog is conjugated to an albumin moiety (e.g., human serum albumin or a portion thereof) or to an albumin binding peptide. Thus in some embodiments a compstatin analog is modified with one or more polypeptide or non-polypeptide components, e.g., the compstatin analog is pegylated or conjugated to another moiety. In some embodiments the component is not the Fc domain of an immunoglobulin or a portion thereof. A compstatin analog can be provided as a multimer or as part of a supramolecular complex, which can include either a single molecular species or multiple different species (e.g., multiple different analogs).

In some embodiments, a PEG or other moiety has an average molecular weight of at least 10 kD, e.g., at least 20 kD, 30 kD, 40 kD, 50 kD, 60 kD, 70 kD, 80 kD, 90 kD, 100 kD, 110 kD, 120 kD, 130 kD, 140 kD, 150 kD, or more in various embodiments. For example, an average molecular weight may be between 10 kD and 100 kD, e.g., about 10 kD, 20 kD, 30 kD, 40 kD, 50 kD, 60 kD, 70 kD, 75 kD, 80 kD, 90 kD, or 100 kD.

In some embodiments, a compstatin analog, e.g., modified with PEG or other moiety, has a half-life at least 3, 5, 7, 10, 20, 30, 50, 75, 100-fold or more as great as that of a compstatin analog having the same peptide sequence but lacking the moiety. For example, a half-life may be between 3 and 100-fold as great as that of a compstatin analog having the same peptide sequence but lacking the moiety, e.g., between 3 and 50-fold as great, between 50 and 100-fold as great, etc.

In some embodiments, a compstatin analog, e.g., modified with PEG or other moiety, has a plasma half-life of at least 1, 2, 3, 4, 5, 6, 7, 10, 14, 21, or 28 days. For example, a compstatin analog, e.g., modified with PEG or other moiety, may have a plasma half-life of between 1 day and 28 days, e.g., between 1 day and 4 days, between 4 days and 7 days, etc.

It will be appreciated that a variety of approaches to determining pharmacokinetic (PK) parameters such as half-life can be used. An appropriate method can be selected by one of ordinary skill in the art. In general, half-life can be determined by a method comprising: administering one or more doses of the compound to subjects, obtaining blood samples from the subject at various times after administration, measuring the concentration of the compound in said samples, and calculating a half-life based at least in part on said measurements. For example, in some embodiments, samples may be obtained at times 0 (pre-dose), 5 min, 15 min, 30 min, 1 hr, 4 hr, 8 hr, 24 hr (1 day), 48 hr (2 days), 96 hr (4 days), 192 hr (8 days), 14 days, 21 days, and 28 days post-dose. It will be appreciated that these time points are exemplary. Different time points and/or more or fewer time points could be used in various embodiments. One of ordinary skill in the art would select appropriate time points. The blood samples are typically processed to obtain plasma or serum prior to making the measurements. Any appropriate method for measuring the compound may be used. For example, in some embodiments an immunoassay is used. In some embodiments, a chromatography-based method is used (e.g., liquid chromatography (LC), liquid chromatography-mass spectrometry (LC-MS) or liquid chromatography-tandem mass spectrometry (LC-MS-MS). In some embodiments, a bioassay is used. In many embodiments, the half-life is a terminal (elimination) half-life. In some embodiments, a terminal half-life is calculated following administration of a single dose. In some embodiments, a terminal half-life is calculated following administration of multiple doses and allowing the concentration to reach steady state. In some embodiments, a half-life determined for the initial (distribution) phase is used. For example, if the majority of the compound is removed from circulation during the distribution phase, an initial half-life may be used in some embodiments.

In some embodiments, half-life is determined by conducting a PK analysis using non-compartmental analysis on multiple dose PK data from a group of subjects. In some embodiments, half-life is determined by conducting a PK analysis using a standard 1-compartment model on multiple dose PK data from a group of subjects. In some embodiments, a half-life is determined in subjects who are healthy and not known to be suffering from a disorder. In some embodiments, a half-life is determined in subjects suffering from a complement-mediated disorder. In some embodiments, a half-life is determined in adults (persons at least 18 years of age). A variety of software tools are available to facilitate calculation of PK parameters. For example, Phoenix NMLE or Phoenix WinNonlin software (PharSight Corp, St. Louis, Mo.) or Kinetica (Thermo Scientific) can be used. It will be appreciated that a reasonable estimate of half-life based on a model can be used.

In some embodiments, a compstatin analog is a multivalent compound comprising a plurality of compstatin analog moieties covalently or noncovalently linked to a polymeric backbone or scaffold. The compstatin analog moieties can be identical or different. In certain embodiments of the invention the multivalent compound comprises multiple instances, or copies, of a single compstatin analog moiety. In other embodiments of the invention the multivalent compound comprises one or more instances of each of two of more non-identical compstatin analog moieties, e.g., 3, 4, 5, or more different compstatin analog moieties. In certain embodiments of the invention the number of compstatin analog moieties ("n") is between 2 and 6. In other embodiments of the invention n is between 7 and 20. In other embodiments of the invention n is between 20 and 100. In other embodiments n is between 100 and 1,000. In other embodiments of the invention n is between 1,000 and 10,000. In other embodiments n is between 10,000 and 50,000. In other embodiments n is between 50,000 and 100,000. In other embodiments n is between 100,000 and 1,000,000. The compstatin analog moieties may be attached directly to the polymeric scaffold or may be attached via a linking moiety that connects the compstatin analog moiety to the polymeric scaffold. The linking moiety may be attached to a single compstatin analog moiety and to the polymeric scaffold. Alternately, a linking moiety may have multiple compstatin analog moieties joined thereto so that the linking moiety attaches multiple compstatin analog moieties to the polymeric scaffold.

In some embodiments, a compstatin analog comprises an amino acid having a side chain comprising a primary or secondary amine, e.g., a Lys residue. For example, any of the compstatin analog sequences disclosed herein may be extended or modified by addition of a linker comprising one or more amino acids, e.g., one or more amino acids comprising a primary or secondary amine, e.g., in a side chain thereof. For example, a Lys residue, or a sequence comprising a Lys residue, is added at the N-terminus and/or C-terminus of the compstatin analog. In some embodiments, the Lys residue is separated from the cyclic portion of the compstatin analog by a rigid or flexible spacer. A linker or spacer may, for example, comprise a substituted or unsubstituted, saturated or unsaturated alkyl chain, oligo(ethylene glycol) chain, and/or other moieties. The length of the chain may be, e.g., between 2 and 20 carbon atoms. In some embodiments the spacer is or comprises a peptide. The peptide spacer may be, e.g., between 1 and 20 amino acids in length, e.g., between 4 and 20 amino acids in length. Suitable spacers can comprise or consist of multiple Gly residues, Ser residues, or both, for example. Optionally, the amino acid having a side chain comprising a primary or secondary amine and/or at least one amino acid in a spacer is a D-amino acid. A PEG moiety or similar molecule or polymeric scaffold may be linked to the primary or secondary amine, optionally via a linker. In some embodiments, a bifunctional linker is used. A bifunctional linker may comprise two reactive functional groups, which may be the same or different in various embodiments. In various embodiments, one or more linkers, spacers, and/or techniques of conjugation described in Hermanson, supra, is used.

Any of a variety of polymeric backbones or scaffolds could be used. For example, the polymeric backbone or scaffold may be a polyamide, polysaccharide, polyanhydride, polyacrylamide, polymethacrylate, polypeptide, polyethylene oxide, or dendrimer. Suitable methods and polymeric backbones are described, e.g., in WO98/46270 (PCT/US98/07171) or WO98/47002 (PCT/US98/06963). In one embodiment, the polymeric backbone or scaffold comprises multiple reactive functional groups, such as carboxylic acids, anhydride, or succinimide groups. The polymeric backbone or scaffold is reacted with the compstatin analogs. In one embodiment, the compstatin analog comprises any of a number of different reactive functional groups, such as carboxylic acids, anhydride, or succinimide groups, which are reacted with appropriate groups on the polymeric backbone. Alternately, monomeric units that could be joined to one another to form a polymeric backbone or scaffold are first reacted with the compstatin analogs and the resulting monomers are polymerized. In another embodiment, short chains are prepolymerized, functionalized, and then a mixture of short chains of different composition are assembled into longer polymers.

Compstatin Mimetics

The structure of compstatin is known in the art, and NMR structures for a number of compstatin analogs having higher activity than compstatin are also known (Malik, supra). Structural information may be used to design compstatin mimetics. In some embodiments, a compstatin mimetic is any compound that competes with compstatin or any compstatin analog (e.g., a compstatin analog whose sequence is set forth in Table 1) for binding to C3 or a fragment thereof (such as a 40 kD fragment of the β chain to which compstatin binds). In some embodiments, the compstatin mimetic has an activity equal to or greater than that of compstatin. In some embodiments, the compstatin mimetic is more stable, orally available, or has a better bioavailability than compstatin. The compstatin mimetic may be a peptide, nucleic acid, or small molecule. In certain embodiments the compstatin mimetic is a compound that binds to the binding site of compstatin as determined in a compstatin-C3 structure, e.g., a crystal structure or a 3-D structure derived from NMR experiments. In certain embodiments the compstatin mimetic is a compound that could substitute for compstatin in a compstatin-C3 structure and would form substantially the same intermolecular contacts with C3 as compstatin. In certain embodiments the compstatin mimetic is a compound that binds to the binding site of a peptide having a sequence set forth in Table 1, e.g., SEQ ID NO: 14, 21, 28, 29, 32, 33, 34, or 36 or in certain embodiments SEQ ID NO: 30 or 31, in a peptide-C3 structure. In certain embodiments the compstatin mimetic is a compound that could substitute for a peptide having a sequence set forth in Table 1, e.g., SEQ ID NO: 14, 21, 28, 29, 32, 33, 34, or 36 or in certain embodiments SEQ ID NO: 30 or 31, in a peptide-C3 structure and would form substantially the same intermolecular contacts with C3 as the peptide. In certain embodiments the compstatin mimetic has a non-peptide backbone but has side chains arranged in a sequence designed based on the sequence of compstatin.

One of skill in the art will appreciate that once a particular desired conformation of a short peptide has been ascertained, methods for designing a peptide or peptidomimetic to fit that conformation are well known. See, e.g., G. R. Marshall (1993), Tetrahedron, 49: 3547-3558; Hruby and Nikiforovich (1991), in Molecular Conformation and Biological Interactions, P. Balaram & S. Ramasehan, eds., Indian Acad. of Sci., Bangalore, PP. 429-455), Eguchi M, Kahn M., Mini Rev Med Chem., 2(5):447-62, 2002. Of particular relevance to the present invention, the design of peptide analogs may be further refined by considering the contribution of various side chains of amino acid residues, e.g., for the effect of functional groups or for steric considerations as described in the art for compstatin and analogs thereof, among others.

It will be appreciated by those of skill in the art that a peptide mimic may serve equally well as a peptide for the purpose of providing the specific backbone conformation and side chain functionalities required for binding to C3 and inhibiting complement activation. Accordingly, it is contemplated as being within the scope of the present invention to produce and utilize C3-binding, complement-inhibiting compounds through the use of either naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic" or "isosteric mimetic," to designate substitutions or derivations of a peptide that possesses much the same backbone conformational features and/or other functionalities, so as to be sufficiently similar to the exemplified peptides to inhibit complement activation. More generally, a compstatin mimetic is any compound that would position pharmacophores similarly to their positioning in compstatin, even if the backbone differs.

The use of peptidomimetics for the development of high-affinity peptide analogs is well known in the art. Assuming rotational constraints similar to those of amino acid residues within a peptide, analogs comprising non-amino acid moieties may be analyzed, and their conformational motifs verified, by means of the Ramachandran plot (Hruby & Nikiforovich 1991), among other known techniques.

One of skill in the art will readily be able to establish suitable screening assays to identify additional compstatin mimetics and to select those having desired inhibitory activities. For example, compstatin or an analog thereof could be labeled (e.g., with a radioactive or fluorescent label) and contacted with C3 in the presence of different concentrations of a test compound. The ability of the test compound to diminish binding of the compstatin analog to C3 is evaluated. A test compound that significantly diminishes binding of the compstatin analog to C3 is a candidate compstatin mimetic. For example, a test compound that diminishes steady-state concentration of a compstatin analog-C3 complex, or that diminishes the rate of formation of a compstatin analog-C3 complex by at least 25%, or by at least 50%, is a candidate compstatin mimetic. One of skill in the art will recognize that a number of variations of this screening assay may be employed. Compounds to be screened include natural products, libraries of aptamers, phage display libraries, compound libraries synthesized using combinatorial chemistry, etc. The invention encompasses synthesizing a combinatorial library of compounds based upon the core sequence described above and screening the library to identify compstatin mimetics. Any of these methods could also be used to identify new compstatin analogs having higher inhibitory activity than compstatin analogs tested thus far.

Pharmaceutical Compositions and Administration

Suitable preparations, e.g., substantially pure preparations of a compstatin analog or other active agent may be combined with pharmaceutically acceptable carriers or vehicles, etc., to produce an appropriate pharmaceutical composition. The term "pharmaceutically acceptable carrier or vehicle" refers to a non-toxic carrier or vehicle that does not destroy the pharmacological activity of the compound with which it is formulated. One of skill in the art will understand that a carrier or vehicle is "non-toxic" if it is compatible with administration to a subject in an amount appropriate to deliver the compound without causing undue toxicity. Pharmaceutically acceptable carriers or vehicles that may be used in the compositions of this invention include, but are not limited to, water, physiological saline, Ringer's solution, 5% dextrose, and the like. The composition may include other components as appropriate for the formulation desired, e.g., as discussed below. Supplementary active compounds, e.g., compounds independently useful for treating a subject suffering from neuropathic pain, including but not limited to the compounds discussed herein, can also be incorporated into the compositions. The invention provides such pharmaceutical compositions comprising a compstatin analog and, optionally, a second active agent useful for treating a subject suffering from neuropathic pain.

A pharmaceutical composition can be administered to a subject by any suitable route of administration including, but not limited to, intravenous, intramuscular, subcutaneously, transdermally, by inhalation, by nasal delivery, intrathecally, intracranially, intraarterially, orally, etc. In some embodiments, a composition comprising a compstatin analog is administered intravenously. In some embodiments, a composition comprising a compstatin analog is administered via a catheter or pump directly into the intrathecal space. In some embodiments, a composition comprising a compstatin analog forms a gel upon administration into the intrathecal space. See PCT/US2008/078593 (WO/2009/046198). It will be understood that "administration" encompasses directly administering a compound or composition to a subject, instructing a third party to administer a compound or composition to a subject, prescribing or suggesting a compound or composition to a subject (e.g., for self-administration), self-administration, and, as appropriate, other means of making a compound or composition available to a subject. In some embodiments, a subject has suffered from neuropathic pain for at least 3, 6, 9, or 12 months. In some embodiments, a subject has a condition that is frequently associated with neuropathic pain, but the subject has not developed neuropathic pain. The compstatin analog is administered prophylactically, to reduce the likelihood that neuropathic pain will develop.

Pharmaceutical compositions suitable for injectable use (e.g., intravenous administration) or by pump or catheter typically include sterile aqueous solutions (where water soluble) or dispersions and sterile powders for the extemporaneous preparation of sterile injectable solutions or dispersion. Sterile solutions can be prepared by incorporating the compound, e.g., compstatin analog in the required amount in an appropriate solvent, optionally with one or a combination of ingredients such as buffers such as acetates, citrates, lactates or phosphates; agents for the adjustment of tonicity such as sodium chloride or dextrose; antibacterial agents such as benzyl alcohol or methyl parabens; antioxidants such as ascorbic acid, glutathione, or sodium bisulfite; chelating agents such as ethylenediaminetetraacetic acid; and other suitable ingredients etc., as desired, followed by filter-based sterilization. One of skill in the art will be aware of numerous physiologically acceptable compounds that may be included in a pharmaceutical composition. Other useful compounds include, for example, carbohydrates, such as glucose, sucrose, lactose; dextrans; amino acids such as glycine; polyols such as mannitol. These compounds may, for example, serve as bulking agents and/or stabilizers, e.g., in a powder and/or when part of the manufacture or storage process involves lyophilization. Surfactant(s) such as Tween-80, Pluronic-F108/F68, deoxycholic acid, phosphatidylcholine, etc., may be included in a composition, e.g., to increase solubility or to provide microemulsion to deliver hydrophobic drugs. pH can be adjusted with acids or bases, such as hydrochloric acid or sodium hydroxide, if desired. The parenteral preparation can be enclosed in ampoules, disposable syringes or infusion bags or multiple dose vials made of glass or plastic. Preferably solutions for injection are sterile and acceptably free of endotoxin.

Generally, dispersions are prepared by incorporating the active compound into a sterile vehicle which contains a basic dispersion medium and appropriate other ingredients from those enumerated above. In the case of sterile powders for the preparation of sterile injectable solutions, methods of preparation can include vacuum drying and freeze-drying which yields a powder of the active ingredient plus any additional desired ingredient, e.g., from a previously sterile-filtered solution thereof. It will be understood that the pharmaceutically acceptable compounds and preparation methods mentioned herein are exemplary and non-limiting. See, e.g., Remington: The Science and Practice of Pharmacy. 21st Edition. Philadelphia, Pa. Lippincott Williams & Wilkins, 2005, for additional discussion of pharmaceutically acceptable compounds and methods of preparing pharmaceutical compositions of various types.

In some embodiments, a compstatin analog or other active agent is prepared as a controlled release formulation, e.g., an implant or microencapsulated delivery system. In some embodiments, a controlled release formulation comprises microparticles or nanoparticles comprising a compstatin analog. Biodegradable, biocompatible polymers can be used, such as ethylene vinyl acetate, polyanhydrides, polyglycolic acid, PLGA, collagen, polyorthoesters, polyethers, and polylactic acid. Methods for preparation of such formulations will be apparent to those skilled in the art. In some embodiments, a controlled release formulation comprises a gel-forming material. Liposomal suspensions can also be used as pharmaceutically acceptable carriers. These can be prepared according to methods known to those skilled in the art, for example, as described in U.S. Pat. No. 4,522,811 and other references listed herein. Liposomes, including targeted liposomes (e.g., antibody targeted liposomes) and pegylated liposomes have been described (Hansen C B, et al., Biochim Biophys Acta. 1239(2):133-44, 1995; Torchilin V P, et al., Biochim Biophys Acta, 1511(2):397-411, 2001; Ishida T, et al., FEBS Lett. 460(1):129-33, 1999). One of ordinary skill in the art will appreciate that the materials and methods selected for preparation of a controlled release formulation, implant, etc., should be such as to retain activity of the compound.

It will be appreciated that the compstatin analog and/or additional active agent(s) can be provided as a pharmaceutically acceptable salt. Pharmaceutically acceptable salts include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Also, pharmaceutically-acceptable salts can be prepared as alkaline metal or alkaline earth salts, such as sodium, potassium or calcium salts, if appropriate depending on the identity of the active agent.

A pharmaceutical composition can be administered in an amount effective to achieve a desired therapeutic effect. A variety of clinical assessment instruments known in the art can be used to assess the severity of neuropathic pain. "Severity" of neuropathic pain can relate to pain intensity, pain unpleasantness, and/or impact of pain on functioning or quality of life, sleep, mood. For example, pain intensity can be rated on a 0-10 rating scale (0=no pain, 10=worst pain imaginable) or using the McGill Pain Questionnaire (0 to 45 scale) or the short form thereof. A visual analog scale (VAS), numerical rating scale (NRS), or verbal rating scale (VRS) may be used. Other assessment tools include, e.g., the Symptom Score Scale (Kvinesdal et al., Imipramine treatment of painful diabetic neuropathy. JAMA 251:1727-1730, 1984), the Neuropathic Pain Scale (Galer B S, Jensen M P (1997). Development and preliminary validation of a pain measure specific to neuropathic pain: the Neuropathic Pain Scale. Neurology 48:332-338, 1997), the Guy/Farrar Patient Global Impression of Change (PGIC) scale, the Multidimensional Pain Inventory (MPI) (Kerns R D, et al., The West Haven-Yale Multidimensional Pain Inventory (WHYMPI). Pain. 23:345-356, 1985), or the Pain Relief Scale (Devers A, Galer B S, Topical lidocaine patch relieves a variety of neuropathic pain conditions: an open-label study. Clin J Pain 16:205-208, 2000). The intensity of the different pain components that a subject may report (spontaneous ongoing pain, spontaneous paroxysmal pain, dysesthesiae and paresthesiae) or the evoked pains (allodynia and hyperalgesia), and/or pain worsening with movement, can be assessed. For example, reduction in characteristics of neuropathic pain such as those assessed in the LANSS scale can be assessed. The impact of pain on functioning or quality of life can be assessed using, e.g., an SF-36 score, Bodily Pain Index Interference score, Oswestry Disability Index score, and/or Euro QoL score. Further non-limiting discussion of outcome measures that could be used is found in, e.g., Dworkin R H, Pain. 113(1-2): 9-19, 2005; Bryce, T N, et al., J Spinal Cord Med. 30(5): 421-440, 2007, guidelines for assessment of neuropathic pain established by the European Federation of Neurological Societies (EFNS) and references in any of the foregoing. In some embodiments, an effective amount produces a statistically significant improvement in pain intensity, physical functioning, quality of life, and/or emotional functioning.

In some embodiments, an effective amount produces significant pain relief, e.g., at least a 20% reduction in pain score. In some embodiments, an effective amount produces at least a 30% reduction in pain score. In some embodiments, an effective amount produces at least a 40% reduction in pain score. In some embodiments, an effective amount produces at least a 50% reduction in pain score. In some embodiments, an effective amount produces a reduction of at least 2, 3, 4, or 5 points in a 10 or 11 point pain intensity scale. In some embodiments, such reduction (e.g., at least 20%, 30%, 40%, 50%, or more, and/or a reduction of at least 2, 3, 4, or 5 points on 10 or 11 point scale) is present in at least 5%, 10%, 20%, or more of a group of subjects treated. In some embodiments, an effective amount results in a better average functional status after 1, 3, or 6 months, in a group of subjects who received a compstatin analog as compared with a group of control subjects.

In some embodiments, treatment with a compstatin analog results in reduced incidence and/or severity of side effects relative to treatment with conventional therapy for neuropathic pain. For example, there may be reduced dizziness, vertigo, somnolence, sedation, fatigue, lethargy, dry mouth, ataxia, gait disturbance, constipation, and/or postural hypotension. In some embodiments, a conventional therapy is a therapy discussed in, Attal, N., et al., EFNS guidelines on pharmacological treatment of neuropathic pain. European Journal of Neurology 2006, 13: 1153-1169, 2006 and/or in Chou R, et al., Drug Class Review on Drugs for Neuropathic Pain. 2007 (available at http://www.ohsu.edu/drugeffectiveness/reports/final.cfm). In some embodiments such conventional therapy is approved by a government agency responsible for regulating pharmaceutical agents, such as the U.S. Food & Drug Administration or the European Medicines Evaluation Agency, for use in treating neuropathic pain.

In accordance with certain embodiments of the invention a pharmaceutical composition comprising a compstatin analog is administered parenterally for treatment of neuropathic pain. In some embodiments, the composition is administered intravenously. In some embodiments, the composition is administered by intravenous injection. In some embodiments the composition is administered as an IV bolus or an IV infusion. In some embodiments the composition is administered as an IV drip. In some embodiments the composition is administered as an IV bolus followed by an IV infusion or IV drip. In some embodiments an IV infusion is administered over about 1, 2, 3, 4, 5, 15, 20, 30, or 60 minutes. In some embodiments an IV drip is administered over more than 60 minutes, e.g., over about 1, 2, 3, or more hours. In some embodiments, a total amount of between about 0.1 mg/kg and about 2,000 mg/kg of compstatin analog is administered, e.g., between about 1 mg/kg and about 1,000 mg/kg, e.g., between about 5 mg/kg and about 500 mg/kg, e.g., within a 24 hour period. In some embodiments, a total amount of between about 10 mg/kg and about 100 mg/kg of compstatin analog is administered, e.g., between about 10 mg/kg and about 50 mg/kg, e.g., between about 10 mg/kg and about 20 mg/kg, e.g., within a 24 hour period.

In some embodiments, the invention provides a compstatin analog or pharmaceutical composition comprising a compstatin analog, packaged together with a package insert (label) approved by a government agency responsible for regulating pharmaceutical agents, e.g., the U.S. Food & Drug Administration, specifying neuropathic pain and/or one or more indication(s) associated with neuropathic pain as indication(s) for which the composition and/or compstatin analog has been approved for use. In some embodiments, a package insert states particular patient and/or disease characteristics or criteria that define a patient population or disease category for treatment of which the composition has been approved for use. In some embodiments, a package insert describes an appropriate dose, dose range, and/or administration route or method for treating a subject suffering from neuropathic pain. In some embodiments, the invention provides a pharmaceutical pack comprising: (a) a compstatin analog in concentrated or solid form (e.g., as a lyophilized powder); (b) a pharmaceutically acceptable carrier, diluent, or vehicle. In some embodiments, a suitable carrier, diluent, or vehicle may be provided separately or acquired by a health care provider from an appropriate source. Optionally a pack or label contains (e.g., in addition to specifying neuropathic pain and/or one or more indication(s) associated with neuropathic pain as indication(s) for which the composition and/or compstatin analog has been approved for use) instructions for dissolving or diluting the compstatin analog in a carrier, diluent, or vehicle to produce a composition for administration.

In some embodiments, a compstatin analog is administered daily. It will be appreciated that a variety of different dosing regimens could be used to administer a desired total daily amount. For example, a desired amount of compstatin analog could be administered in a single administration or in multiple administrations, e.g., during a 24 hour period. For example, a subject could receive two doses within a 24 hour period, which doses could be administered over the same length of time or over different lengths of time. In some embodiments, a compstatin analog is administered at time intervals greater than 24 hours. For example, doses could be administered on average every other day, every 3-4 days, weekly, every 10 days, every 2 weeks, monthly, etc. Treatment can continue for, e.g., months, years, or indefinitely.

The invention encompasses administration of a compstatin analog in combination with additional therapy. Such additional therapy may include, but is not limited to, administration of any agent(s) used in the art or potentially useful for treating a subject suffering from neuropathic pain and/or suffering from a condition associated with neuropathic pain. Examples include, e.g., antidepressants (e.g., SSRIs, TCAs), anticonvulsants, NMDA antagonists, topical anesthetics or other topical agents (e.g., lidocaine, capsaicin), opioid analgesics, sodium channel blockers, etc. See, e.g., Chou R, et al., Drug Class Review on Drugs for Neuropathic Pain. 2007 (available at http://www.ohsu.edu/drugeffectiveness/reports/final.cfm), Gilron, I., et al., CMAJ, 175(3): 265-275, 2006; and/or Attal N, et al., Eur J Neurol. 2010 Apr. 9. [Epub ahead of print].

When two or more therapies (e.g., compounds or compositions) are used or administered "in combination" with each other, they may, for example, be given at the same time, within overlapping time periods, or sequentially (e.g., separated by up to about 2, 4, or 6 weeks in time, or more), in various embodiments of the invention. They may be administered via the same route or different routes. In some embodiments, the compounds or compositions are administered within 48 hours of each other. In some embodiments, a compstatin analog can be given prior to or after administration of the additional compound(s), e.g., sufficiently close in time that the compstatin analog and additional compound(s) are present at useful levels within the body at least once. In some embodiments, the compounds or compositions are administered sufficiently close together in time such that no more than 90% of the earlier administered composition has been metabolized to inactive metabolites or eliminated, e.g., excreted, from the body, at the time the second compound or composition is administered.

In some embodiments, a composition that includes both the compstatin analog and additional compound(s) is administered. In some aspects, the invention provides a composition comprising a compstatin analog and a second agent useful for treating neuropathic pain and/or for treating a condition associated with neuropathic pain.

One of skill in the art can select an appropriate amount and/or dose of other agent(s) described herein that may be used in conjunction with a compstatin analog. For example, e.g., in some embodiments an amount or dose ranging from about 0.001 mg/kg to 1,000 mg/kg body weight, e.g., about 0.01 to 25 mg/kg body weight, e.g., about 0.1 to 20 mg/kg body weight, e.g., about 1 to 10 mg/kg of a compound described herein is administered at various intervals and over different periods of time as appropriate. The skilled artisan will appreciate that certain factors can influence the total amount, dosage(s) and timing required to effectively treat a subject, including but not limited to the severity of the pain, other treatments being administered, the general health and/or age of the subject, and diseases that may be present.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. It will be appreciated that the invention is in no way dependent upon particular results achieved in any specific example or with any specific embodiment. In the claims articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. For example, and without limitation, it is understood that where claims or description indicate that a residue at a particular position may be selected from a particular group of amino acids or amino acid analogs, the invention includes individual embodiments in which the residue at that position is any of the listed amino acids or amino acid analogs. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims and/or relevant description herein is introduced into another claim. For example, any claim that is dependent on another claim can be modified to include one or more elements, limitations, clauses, or descriptive terms, found in any other claim that is dependent on the same base claim. Furthermore, where the claims recite a composition, it is to be understood that methods of administering the composition according to any of the methods disclosed herein, and methods of using the composition for any of the purposes disclosed herein are included within the scope of the invention, and methods of making the composition according to any of the methods of making disclosed herein are included within the scope of the invention, unless otherwise indicated or unless it would be evident to one of ordinary skill in the art that a contradiction or inconsistency would arise. Methods of treating a subject can include a step of providing a subject in need of such treatment (e.g., a subject who has neuropathic pain or a condition associated with neuropathic pain, has had neuropathic pain or a condition associated with neuropathic pain, or is at increased risk of having or developing neuropathic pain or a condition associated with neuropathic pain), a step of diagnosing a subject as having neuropathic pain or as having a condition associated with neuropathic pain or increased risk of neuropathic pain, and/or a step of selecting a subject for treatment with a compstatin analog, e.g., as a result of the subject suffering from neuropathic pain or a condition associated with neuropathic pain. In some embodiments, increased risk is at least 1.5-fold, e.g., at least 2-fold the risk of an average subject, e.g., a subject reasonably matched at least with regard to one or more characteristics such as age, gender, etc.

Where elements are presented as lists, e.g., in Markush group format, it is to be understood that each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. In addition, it is to be understood that any particular embodiment, aspect, element, feature, etc., of the present invention may be explicitly excluded from any one or more of the claims even if such exclusion is not set forth explicitly herein.

We claim:

1. A method of treating a subject in need of treatment for neuropathic pain, the method comprising:
    administering a therapeutically effective amount of a compstatin analog to the subject,
        wherein the compstatin analog is a compound that comprises a cyclic peptide having an amino acid sequence:
Xaa1-Cys-Val-Xaa2-Gln-Asp-Xaa2*-Gly-Xaa3-His-Arg-Cys-Xaa4 (SEQ ID NO: 6); wherein:
Xaa1 is Ile, Val, Leu, B$^1$-Ile, B$^1$-Val, B$^1$-Leu or a dipeptide comprising Gly-Ile or B$^1$-Gly-Ile, and B$^1$ represents a first blocking moiety;
Xaa2 is 1-methyltryptophan;
Xaa2* is Trp or an analog of Trp;
Xaa3 is His, Ala or an analog of Ala, Phe, Trp, or an analog of Trp;
Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of the L-Thr, D-Thr, Ile, Val, Gly, Ala, or Asn optionally is replaced by a second blocking moiety B$^2$; and
the two Cys residues are joined by a disulfide bond.

2. The method of claim 1, wherein the compstatin analog is administered intravenously.

3. The method of claim 1, wherein the activity of the compstatin analog is at least 100 times as great as the activity of compstatin as measured in an in vitro assay.

4. The method of claim 1, wherein
Xaa1 is Ile, Val, Leu, Ac-Ile, Ac-Val, Ac-Leu or a dipeptide comprising Gly-Ile or Ac-Gly-Ile.

5. The method of claim 1, wherein Xaa2* is an analog of Trp having an electronegative substituent on the indole ring and not having increased hydrophobic character relative to Trp.

6. The method of claim 1, wherein the compstatin analog has the sequence of SEQ ID NO: 28 or 32.

7. The method of claim 1, wherein the peptide is acetylated at the N-terminus, amidated at the C-terminus, or both acetylated at the N-terminus and amidated at the C-terminus.

8. The method of claim 1, further comprising: administering an additional therapy for neuropathic pain to the subject, wherein the additional therapy is selected from the group consisting of antidepressants, anticonvulsants, NMDA antagonists, topical anesthetics, opioid analgesics, and sodium channel blockers.

9. The method of claim 1, wherein Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of the L-Thr, D-Thr, Ile, Val, Gly, Ala, or Asn is replaced by —NH$_2$.

* * * * *

SEQUENCE LISTING

```
<160> NUMBER OF SEQ ID NOS: 36

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (2)..(12)

<400> SEQUENCE: 1

Ile Cys Val Val Gln Asp Trp Gly His His Arg Cys Thr
1               5                   10

<210> SEQ ID NO 2
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (1)..(19)
<223> OTHER INFORMATION: Any independently selected amino acid or amino
      acid analog
<220> FEATURE:
<221> NAME/KEY: misc_feature
<222> LOCATION: (1)..(19)
<223> OTHER INFORMATION: This region may encompass 2 to 19 residues,
      wherein some residues may be absent
<220> FEATURE:
```

```
<221> NAME/KEY: VARIANT
<222> LOCATION: (22)..(22)
<223> OTHER INFORMATION: Trp or an analog of Trp
<220> FEATURE:
<221> NAME/KEY: VARIANT
<222> LOCATION: (24)..(42)
<223> OTHER INFORMATION: Any independently selected amino acid or amino
      acid analog
<220> FEATURE:
<221> NAME/KEY: misc_feature
<222> LOCATION: (24)..(42)
<223> OTHER INFORMATION: This region may encompass 2 to 19 residues,
      wherein some residues may be absent

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Gln Asp Xaa Gly Xaa Xaa Xaa Xaa Xaa Xaa Xaa Xaa
            20                  25                  30

Xaa Xaa Xaa Xaa Xaa Xaa Xaa Xaa Xaa Xaa
        35                  40

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: see specification as filed for detailed
      description of substitutions and preferred embodiments
<220> FEATURE:
<221> NAME/KEY: VARIANT
<222> LOCATION: (1)..(1)
<223> OTHER INFORMATION: Trp or an analog of Trp
<220> FEATURE:
<221> NAME/KEY: VARIANT
<222> LOCATION: (4)..(4)
<223> OTHER INFORMATION: Trp or an analog of Trp

<400> SEQUENCE: 3

Xaa Gln Asp Xaa Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: see specification as filed for detailed
      description of substitutions and preferred embodiments
<220> FEATURE:
<221> NAME/KEY: VARIANT
<222> LOCATION: (1)..(1)
<223> OTHER INFORMATION: Trp or an analog of Trp
<220> FEATURE:
<221> NAME/KEY: VARIANT
<222> LOCATION: (4)..(4)
<223> OTHER INFORMATION: Trp or an analog of Trp
<220> FEATURE:
<221> NAME/KEY: VARIANT
<222> LOCATION: (6)..(6)
<223> OTHER INFORMATION: His, Ala, analogs of Ala, Phe or Trp

<400> SEQUENCE: 4

Xaa Gln Asp Xaa Gly Xaa
```

-continued

```
<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: see specification as filed for detailed
      description of substitutions and preferred embodiments
<220> FEATURE:
<221> NAME/KEY: VARIANT
<222> LOCATION: (1)..(3)
<223> OTHER INFORMATION: Any independently selected amino acid or amino
      acid analog
<220> FEATURE:
<221> NAME/KEY: VARIANT
<222> LOCATION: (4)..(4)
<223> OTHER INFORMATION: Trp or analog of Trp
<220> FEATURE:
<221> NAME/KEY: VARIANT
<222> LOCATION: (7)..(7)
<223> OTHER INFORMATION: Trp or analog of Trp
<220> FEATURE:
<221> NAME/KEY: VARIANT
<222> LOCATION: (9)..(13)
<223> OTHER INFORMATION: Any independently selected amino acid or amino
      acid analog

<400> SEQUENCE: 5

Xaa Xaa Xaa Xaa Gln Asp Xaa Gly Xaa Xaa Xaa Xaa Xaa
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: see specification as filed for detailed
      description of substitutions and preferred embodiments
<220> FEATURE:
<221> NAME/KEY: VARIANT
<222> LOCATION: (1)..(2)
<223> OTHER INFORMATION: Ile, Val, Leu, B1-Ile, B1-Val, B1-Leu or a
      dipeptide comprising Gly-Ile or B1-Gly-Ile, wherein B1 represents
      a first blocking moiety
<220> FEATURE:
<221> NAME/KEY: misc_feature
<222> LOCATION: (1)..(2)
<223> OTHER INFORMATION: This region may encompass 1 to 2 residues,
      wherein some positions may be absent
<220> FEATURE:
<221> NAME/KEY: DISULFID
<222> LOCATION: (3)..(13)
<220> FEATURE:
<221> NAME/KEY: VARIANT
<222> LOCATION: (5)..(5)
<223> OTHER INFORMATION: Independently selected from Trp or analogs of
      Trp
<220> FEATURE:
<221> NAME/KEY: VARIANT
<222> LOCATION: (8)..(8)
<223> OTHER INFORMATION: Independently selected from Trp or analogs of
      Trp
<220> FEATURE:
<221> NAME/KEY: VARIANT
<222> LOCATION: (10)..(10)
<223> OTHER INFORMATION: His, Ala or an analog of Ala, Phe, Trp or an
      analog of Trp
```

```
<220> FEATURE:
<221> NAME/KEY: VARIANT
<222> LOCATION: (14)..(16)
<223> OTHER INFORMATION: L-Thr, D-Thr, Ile, Val, Gly, a dipeptide
      selected from Thr-Ala and Thr-Asn, or a tripeptide comprising
      Thr-Ala-Asn, wherein a C-terminal -OH of any of the L-Thr, D-Thr,
      Ile, Val, Gly, Ala or Asn is optionally replaced by a second
      blocking moiety
<220> FEATURE:
<221> NAME/KEY: misc_feature
<222> LOCATION: (14)..(16)
<223> OTHER INFORMATION: This region may encompass 1 to 3 residues,
      wherein some positions may be absent

<400> SEQUENCE: 6

Xaa Xaa Cys Val Xaa Gln Asp Xaa Gly Xaa His Arg Cys Xaa Xaa Xaa
 1               5                  10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<223> OTHER INFORMATION: see specification as filed for detailed
      description of substitutions and preferred embodiments
<220> FEATURE:
<221> NAME/KEY: VARIANT
<222> LOCATION: (1)..(2)
<223> OTHER INFORMATION: Ile, Val, Leu, Ac-Ile, Ac-Val, Ac-Leu or a
      dipeptide comprising Gly-Ile or Ac-Gly-Ile
<220> FEATURE:
<221> NAME/KEY: misc_feature
<222> LOCATION: (1)..(2)
<223> OTHER INFORMATION: This region may encompass 1 to 2 residues,
      wherein some positions may be absent
<220> FEATURE:
<221> NAME/KEY: DISULFID
<222> LOCATION: (3)..(13)
<220> FEATURE:
<221> NAME/KEY: VARIANT
<222> LOCATION: (5)..(5)
<223> OTHER INFORMATION: Independently selected from Trp or analogs of
      Trp
<220> FEATURE:
<221> NAME/KEY: VARIANT
<222> LOCATION: (8)..(8)
<223> OTHER INFORMATION: Independently selected from Trp or analogs of
      Trp
<220> FEATURE:
<221> NAME/KEY: VARIANT
<222> LOCATION: (10)..(10)
<223> OTHER INFORMATION: His, Ala or an analog of Ala, Phe, Trp or an
      analog of Trp
<220> FEATURE:
<221> NAME/KEY: VARIANT
<222> LOCATION: (14)..(16)
<223> OTHER INFORMATION: L-Thr, D-Thr, Ile, Val, Gly, a dipeptide
      selected from Thr-Ala or Thr-Asn, or a tripeptide comprising
      Thr-Ala-Asn, wherein a c-term -OH of any of L-Thr, D-Thr, Ile,
      Val, Gly, Ala, or Asn is optionally replaced by -NH2
<220> FEATURE:
<221> NAME/KEY: misc_feature
<222> LOCATION: (14)..(16)
<223> OTHER INFORMATION: This region may encompass 1 to 3 residues,
      wherein some positions may be absent

<400> SEQUENCE: 7

Xaa Xaa Cys Val Xaa Gln Asp Xaa Gly Xaa His Arg Cys Xaa Xaa Xaa
 1               5                  10                  15

<210> SEQ ID NO 8
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal H
<220> FEATURE:
<221> NAME/KEY: MOD_RES
<222> LOCATION: (13)..(13)
<223> OTHER INFORMATION: C-terminal CONH2

<400> SEQUENCE: 8

Ile Cys Val Val Gln Asp Trp Gly His His Arg Cys Thr
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (13)..(13)
<223> OTHER INFORMATION: C-terminal CONH2

<400> SEQUENCE: 9

Ile Cys Val Val Gln Asp Trp Gly His His Arg Cys Thr
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (13)..(13)
<223> OTHER INFORMATION: C-terminal CONH2

<400> SEQUENCE: 10

Ile Cys Val Tyr Gln Asp Trp Gly Ala His Arg Cys Thr
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (13)..(13)
```

<223> OTHER INFORMATION: C-terminal COOH

<400> SEQUENCE: 11

Ile Cys Val Trp Gln Asp Trp Gly Ala His Arg Cys Thr
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (13)..(13)
<223> OTHER INFORMATION: C-terminal CONH2

<400> SEQUENCE: 12

Ile Cys Val Trp Gln Asp Trp Gly Ala His Arg Cys Thr
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (13)..(13)
<223> OTHER INFORMATION: d-Thr
<220> FEATURE:
<221> NAME/KEY: MOD_RES
<222> LOCATION: (13)..(13)
<223> OTHER INFORMATION: C-terminal COOH

<400> SEQUENCE: 13

Ile Cys Val Trp Gln Asp Trp Gly Ala His Arg Cys Thr
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 2-napthylalanine
<220> FEATURE:
<221> NAME/KEY: MOD_RES
<222> LOCATION: (13)..(13)
<223> OTHER INFORMATION: C-terminal CONH2

<400> SEQUENCE: 14

Ile Cys Val Ala Gln Asp Trp Gly Ala His Arg Cys Thr

```
1               5                   10
```

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 2-naphthylalanine
<220> FEATURE:
<221> NAME/KEY: MOD_RES
<222> LOCATION: (13)..(13)
<223> OTHER INFORMATION: C-terminal COOH

<400> SEQUENCE: 15

```
Ile Cys Val Ala Gln Asp Trp Gly Ala His Arg Cys Thr
1               5                   10
```

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 1-naphthylalanine
<220> FEATURE:
<221> NAME/KEY: MOD_RES
<222> LOCATION: (13)..(13)
<223> OTHER INFORMATION: C-terminal COOH

<400> SEQUENCE: 16

```
Ile Cys Val Ala Gln Asp Trp Gly Ala His Arg Cys Thr
1               5                   10
```

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 2-indanylglycine carboxylic acid
<220> FEATURE:
<221> NAME/KEY: MOD_RES
<222> LOCATION: (13)..(13)
<223> OTHER INFORMATION: C-terminal CONH2

<400> SEQUENCE: 17

```
Ile Cys Val Gly Gln Asp Trp Gly Ala His Arg Cys Thr
1               5                   10
```

```
<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 2-indanylglycine carboxylic acid
<220> FEATURE:
<221> NAME/KEY: MOD_RES
<222> LOCATION: (13)..(13)
<223> OTHER INFORMATION: C-terminal COOH

<400> SEQUENCE: 18

Ile Cys Val Gly Gln Asp Trp Gly Ala His Arg Cys Thr
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATOIN
<220> FEATURE:
<221> NAME/KEY: MOD_RES
<222> LOCATION: (4)..(4)
<223> OTHER INFORMATION: dihydrotrpytophan
<220> FEATURE:
<221> NAME/KEY: MISC_FEATURE
<222> LOCATION: (13)..(13)
<223> OTHER INFORMATION: C-terminal COOH

<400> SEQUENCE: 19

Ile Cys Val Trp Gln Asp Trp Gly Ala His Arg Cys Thr
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 4-benzoyl-L-phenylalanine
<220> FEATURE:
<221> NAME/KEY: MOD_RES
<222> LOCATION: (13)..(13)
<223> OTHER INFORMATION: C-terminal COOH

<400> SEQUENCE: 20

Ile Cys Val Phe Gln Asp Trp Gly Ala His Arg Cys Thr
1               5                   10
```

```
<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: p-benzoyl-L-phenylalanine
<220> FEATURE:
<221> NAME/KEY: MOD_RES
<222> LOCATION: (13)..(13)
<223> OTHER INFORMATION: C-terminal CONH2

<400> SEQUENCE: 21

Ile Cys Val Phe Gln Asp Trp Gly Ala His Arg Cys Thr
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: Bta
<220> FEATURE:
<221> NAME/KEY: MOD_RES
<222> LOCATION: (13)..(13)
<223> OTHER INFORMATION: C-terminal COOH

<400> SEQUENCE: 22

Ile Cys Val Xaa Gln Asp Trp Gly Ala His Arg Cys Thr
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: Bta
<220> FEATURE:
<221> NAME/KEY: MOD_RES
<222> LOCATION: (13)..(13)
<223> OTHER INFORMATION: C-terminal CONH2

<400> SEQUENCE: 23

Ile Cys Val Xaa Gln Asp Trp Gly Ala His Arg Cys Thr
1               5                   10
```

```
<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (9)..(9)
<223> OTHER INFORMATION: 2-alpha-aminobutyric acid
<220> FEATURE:
<221> NAME/KEY: MOD_RES
<222> LOCATION: (13)..(13)
<223> OTHER INFORMATION: C-terminal CONH2

<400> SEQUENCE: 24

Ile Cys Val Trp Gln Asp Trp Gly Xaa His Arg Cys Thr
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal H
<220> FEATURE:
<221> NAME/KEY: MOD_RES
<222> LOCATION: (16)..(16)
<223> OTHER INFORMATION: C-terminal COOH

<400> SEQUENCE: 25

Gly Ile Cys Val Trp Gln Asp Trp Gly Ala His Arg Cys Thr Ala Asn
1               5                   10                  15

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 5-fluoro-L-tryptophan
<220> FEATURE:
<221> NAME/KEY: MOD_RES
<222> LOCATION: (13)..(13)
<223> OTHER INFORMATION: C-terminal CONH2

<400> SEQUENCE: 26

Ile Cys Val Trp Gln Asp Trp Gly Ala His Arg Cys Thr
1               5                   10

<210> SEQ ID NO 27
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 5-methyl-L-tryptophan
<220> FEATURE:
<221> NAME/KEY: MOD_RES
<222> LOCATION: (13)..(13)
<223> OTHER INFORMATION: C-terminal CONH2

<400> SEQUENCE: 27

Ile Cys Val Trp Gln Asp Trp Gly Ala His Arg Cys Thr
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal Ac
<220> FEATURE:
<221> NAME/KEY: MOD_RES
<222> LOCATION: (4)..(4)
<223> OTHER INFORMATION: 1-methyl-L-tryptophan
<220> FEATURE:
<221> NAME/KEY: MOD_RES
<222> LOCATION: (13)..(13)
<223> OTHER INFORMATION: C-terminal CONH2

<400> SEQUENCE: 28

Ile Cys Val Trp Gln Asp Trp Gly Ala His Arg Cys Thr
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (7)..(7)
<223> OTHER INFORMATION: 5-fluoro-L-tryptophan
<220> FEATURE:
<221> NAME/KEY: MOD_RES
<222> LOCATION: (13)..(13)
<223> OTHER INFORMATION: C-terminal CONH2

<400> SEQUENCE: 29

Ile Cys Val Trp Gln Asp Trp Gly Ala His Arg Cys Thr
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
```

```
                        peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 5-fluoro-L-tryptophan
<220> FEATURE:
<221> NAME/KEY: MOD_RES
<222> LOCATION: (7)..(7)
<223> OTHER INFORMATION: 5-fluoro-L-tryptophan
<220> FEATURE:
<221> NAME/KEY: MOD_RES
<222> LOCATION: (13)..(13)
<223> OTHER INFORMATION: C-terminal CONH2

<400> SEQUENCE: 30

Ile Cys Val Trp Gln Asp Trp Gly Ala His Arg Cys Thr
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 5-methyl-L-tryptophan
<220> FEATURE:
<221> NAME/KEY: MOD_RES
<222> LOCATION: (7)..(7)
<223> OTHER INFORMATION: 5-fluoro-L-tryptophan
<220> FEATURE:
<221> NAME/KEY: MOD_RES
<222> LOCATION: (13)..(13)
<223> OTHER INFORMATION: C-terminal CONH2

<400> SEQUENCE: 31

Ile Cys Val Trp Gln Asp Trp Gly Ala His Arg Cys Thr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 1-methyl-L-tryptophan
<220> FEATURE:
<221> NAME/KEY: MOD_RES
<222> LOCATION: (7)..(7)
<223> OTHER INFORMATION: 5-fluoro-L-tryptophan
<220> FEATURE:
<221> NAME/KEY: MOD_RES
<222> LOCATION: (13)..(13)
<223> OTHER INFORMATION: C-terminal CONH2

<400> SEQUENCE: 32
```

```
Ile Cys Val Trp Gln Asp Trp Gly Ala His Arg Cys Thr
1               5                   10
```

```
<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-term H
<220> FEATURE:
<221> NAME/KEY: MOD_RES
<222> LOCATION: (5)..(5)
<223> OTHER INFORMATION: 6-fluoro-L-tryptophan
<220> FEATURE:
<221> NAME/KEY: MOD_RES
<222> LOCATION: (8)..(8)
<223> OTHER INFORMATION: 6-fluoro-L-tryptophan
<220> FEATURE:
<221> NAME/KEY: MOD_RES
<222> LOCATION: (15)..(15)
<223> OTHER INFORMATION: C-terminal COOH

<400> SEQUENCE: 33

Gly Ile Cys Val Trp Gln Asp Trp Gly Ala His Arg Cys Thr Asn
1               5                   10                  15

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal ACETYLATION
<220> FEATURE:
<221> NAME/KEY: MOD_RES
<222> LOCATION: (4)..(4)
<223> OTHER INFORMATION: 1-formyl-Trp
<220> FEATURE:
<221> NAME/KEY: MOD_RES
<222> LOCATION: (13)..(13)
<223> OTHER INFORMATION: C-terminal CONH2

<400> SEQUENCE: 34

Ile Cys Val Trp Gln Asp Trp Gly Ala His Arg Cys Thr
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: MOD_RES
<222> LOCATION: (4)..(4)
<223> OTHER INFORMATION: 1-methoxy-tryptophan
<220> FEATURE:
<221> NAME/KEY: MISC_FEATURE
<222> LOCATION: (13)..(13)
```

```
<223> OTHER INFORMATION: C-terminal CONH2

<400> SEQUENCE: 35

Ile Cys Val Trp Gln Asp Trp Gly Ala His Arg Cys Thr
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-term H
<220> FEATURE:
<221> NAME/KEY: MOD_RES
<222> LOCATION: (5)..(5)
<223> OTHER INFORMATION: 5-fluoro-L-tryptophan
<220> FEATURE:
<221> NAME/KEY: MOD_RES
<222> LOCATION: (8)..(8)
<223> OTHER INFORMATION: 5-fluoro-L-tryptophan
<220> FEATURE:
<221> NAME/KEY: MOD_RES
<222> LOCATION: (15)..(15)
<223> OTHER INFORMATION: C-terminal COOH

<400> SEQUENCE: 36

Gly Ile Cys Val Trp Gln Asp Trp Gly Ala His Arg Cys Thr Asn
1               5                   10                  15
```